United States Patent
Ruege et al.

(10) Patent No.: US 9,880,110 B2
(45) Date of Patent: *Jan. 30, 2018

(54) MATERIAL EROSION MONITORING SYSTEM AND METHOD

(71) Applicant: PaneraTech, Inc., Chantilly, VA (US)

(72) Inventors: Alexander C. Ruege, Fairfax, VA (US); Yakup Bayram, Falls Church, VA (US)

(73) Assignee: PANERATECH, INC., Chantilly, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/346,161

(22) Filed: Nov. 8, 2016

(65) Prior Publication Data

US 2017/0234808 A1    Aug. 17, 2017

Related U.S. Application Data

(63) Continuation-in-part of application No. 14/226,102, filed on Mar. 26, 2014, now Pat. No. 9,488,601.

(51) Int. Cl.
   *G01N 22/02* (2006.01)
   *G01B 15/02* (2006.01)
   (Continued)

(52) U.S. Cl.
   CPC ......... *G01N 22/02* (2013.01); *F27D 21/0021* (2013.01); *G01B 15/02* (2013.01); *G01N 33/386* (2013.01); *G01N 33/388* (2013.01)

(58) Field of Classification Search
   None
   See application file for complete search history.

(56) References Cited

U.S. PATENT DOCUMENTS

| | | | |
|---|---|---|---|
| 3,562,642 | A | 2/1971 | Hochschild |
| 3,775,765 | A | 11/1973 | Di Piazza et al. |

(Continued)

FOREIGN PATENT DOCUMENTS

| | | |
|---|---|---|
| JP | 2006153845 | 6/2006 |
| JP | 2010-41730 | 2/2010 |

(Continued)

OTHER PUBLICATIONS

Fleischmann, Bernard. "Non-destructive testing of refractories, especially AZS materials, with ultrasound, microwaves, and y-radiation." Glastech. Ber. Glass Sci. Technol. 68 (1995) No. 8.

(Continued)

*Primary Examiner* — Jermele M Hollington
*Assistant Examiner* — Suresh K Rajaputra
(74) *Attorney, Agent, or Firm* — Whiteford, Taylor & Preston, LLP; Gregory M. Stone

(57) ABSTRACT

Disclosed is an improved system and method to evaluate the status of a material. The system and method are operative to identify flaws and measure the erosion profile and thickness of different materials, including refractory materials, using electromagnetic waves. The system is designed to reduce a plurality of reflections, associated with the propagation of electromagnetic waves launched into the material under evaluation, by a sufficient extent so as to enable detection of electromagnetic waves of interest reflected from remote discontinuities of the material. Furthermore, the system and method utilize a configuration and signal processing techniques that reduce clutter and enable the isolation of electromagnetic waves of interest. Moreover, the launcher is impedance matched to the material under evaluation, and the feeding mechanism is designed to mitigate multiple reflection effects to further suppress clutter.

39 Claims, 8 Drawing Sheets

(51) Int. Cl.
*F27D 21/00* (2006.01)
*G01N 33/38* (2006.01)

(56) References Cited

U.S. PATENT DOCUMENTS

| | | | |
|---|---|---|---|
| 4,042,935 | A | 8/1977 | Ajioka |
| 4,107,244 | A | 8/1978 | Ochiai et al. |
| 4,269,397 | A | 5/1981 | Strimple et al. |
| 4,344,030 | A | 8/1982 | Anderson et al. |
| 4,708,482 | A | 11/1987 | Neiheisel |
| 5,212,738 | A | 5/1993 | Chande et al. |
| 5,333,493 | A | 8/1994 | Cutmore |
| 5,363,106 | A | 11/1994 | Hosoda et al. |
| 5,384,543 | A | 1/1995 | Bible et al. |
| 5,502,394 | A | 3/1996 | Piau |
| 5,504,490 | A | 4/1996 | Brendle et al. |
| 5,539,322 | A | 7/1996 | Zoughi et al. |
| 5,574,379 | A | 11/1996 | Darling |
| 5,652,522 | A | 7/1997 | Kates et al. |
| 5,748,003 | A | 5/1998 | Zoughi et al. |
| 5,859,535 | A | 1/1999 | Liu |
| 5,939,889 | A | 8/1999 | Zoughi et al. |
| 5,955,671 | A | 9/1999 | Gilmore et al. |
| 6,172,510 | B1 | 1/2001 | Liu |
| 6,198,293 | B1 | 3/2001 | Woskov et al. |
| 6,480,141 | B1 | 11/2002 | Toth et al. |
| 9,255,794 | B2 | 2/2016 | Walton et al. |
| 9,488,601 | B2 * | 11/2016 | Ruege ............... G01B 15/02 |
| 2002/0158368 | A1 | 10/2002 | Wirth |
| 2004/0095074 | A1 | 5/2004 | Ishii et al. |
| 2004/0169572 | A1 | 9/2004 | Elmore |
| 2004/0177692 | A1 | 9/2004 | Sadri et al. |
| 2005/0007121 | A1 | 1/2005 | Burnett et al. |
| 2005/0133192 | A1 | 6/2005 | Meszaros et al. |
| 2006/0256025 | A1 | 11/2006 | Askildsen et al. |
| 2008/0185903 | A1 | 8/2008 | Bausov |
| 2008/0252293 | A1 | 10/2008 | Lagae et al. |
| 2009/0033578 | A1 | 2/2009 | Martek et al. |
| 2009/0066344 | A1 | 3/2009 | Bray et al. |
| 2009/0179152 | A1 | 7/2009 | Ellison |
| 2009/0302865 | A1 | 12/2009 | Cristini |
| 2010/0033391 | A1 | 2/2010 | McLean |
| 2010/0095740 | A1 | 4/2010 | Walton et al. |
| 2010/0123467 | A1 | 5/2010 | Andarawis et al. |
| 2010/0213922 | A1 | 8/2010 | Sadri et al. |
| 2010/0265117 | A1 | 10/2010 | Weiss |
| 2011/0050248 | A1 | 3/2011 | Bray et al. |
| 2011/0272865 | A1 | 11/2011 | Shameli et al. |
| 2013/0144554 | A1 | 6/2013 | Walton et al. |
| 2013/0268237 | A1 | 10/2013 | Wolfe et al. |
| 2014/0105249 | A1 | 4/2014 | Yastumoi et al. |
| 2015/0276577 | A1 | 10/2015 | Ruege et al. |
| 2015/0362439 | A1 | 12/2015 | Bayram et al. |

FOREIGN PATENT DOCUMENTS

| | | |
|---|---|---|
| JP | 2012013512 | 1/2012 |
| WO | 2013086126 | 6/2013 |
| WO | 2015147827 | 10/2015 |

OTHER PUBLICATIONS

Fleischmann, Bernard. "Ultrasonic determination of the residual wall thickness of glass furnace refractories." Glastech. Ber. Glass Sci. Technol. 70 (1997) No. 1.
Hobson, G.S., et al. "Microwave Measurement of Furnace Wall Thickness." Microwave Conference, 17th European (Sep. 7-11, 1987). pp. 881-886.
Rees, J., et al. "Microwave measurement of furnace wall thickness." Trans Inst M C vol. 8, No. 2, Apr.-Jun. 1986. pp. 91-99.
Supplementary European Search Report issued in co-pending application No. 14886894.6 dated Aug. 17, 2017.
International Search Report issued in co-pending application No. PCT/US2014/031981 dated Aug. 11, 2014.
International Search Report issued in co-pending application No. PCT/US2017/029309 dated Jul. 10, 2017.

* cited by examiner

MATERIAL EROSION MONITORING SYSTEM AND METHOD

CROSS REFERENCE TO RELATED APPLICATION

This application is a continuation-in-part application of U.S. patent application Ser. No. 14/226,102, filed on Mar. 26, 2014, which is hereby incorporated by reference.

FIELD OF THE INVENTION

The present invention relates to systems and methods for evaluating the status of a material. More particularly, the present invention relates to systems and methods for determining refractory bricks-material interface using electromagnetic waves.

BACKGROUND OF THE INVENTION

Evaluation methods and systems exist within various industries for measuring the properties during and after formation of certain materials. The surface characteristics, internal homogeneity, and thickness of a material are some of the important attributes that may require evaluation. In particular, the wall thickness of glass and plastic containers using non-contact reflective and/or absorptive techniques by deploying sensors and emitters to direct radiation towards the container have been addressed in the prior art, as described in U.S. Pat. App. No. 20130268237 by Wolfe et al. However, these methods are primarily aimed to evaluate the thickness of manufactured glass and plastic containers by means of using radiation capable to pass through those materials without sustaining significant losses in the levels of such radiation or accessing more than just one external surface of such materials.

On a bigger scale, some industries such as the glass, steel, and plastic industries use large furnaces to melt the raw material used for processing. These furnaces may reach a length equivalent to the height of a 20-story building. Thus, they are a key asset for manufacturers in terms of costs and operational functionality. In order to minimize the internal heat loss at high operating temperatures, these furnaces are constructed using refractory material, having very high melting temperatures and good insulation properties, to create a refractory melting chamber. However, the inner walls of the refractory chamber of the furnace will degrade during operation. The effects of this degradation include inner surface erosion, stress cracks, and refractory material diffusion into the molten material.

Currently, there is no well-established method of deterministically measuring the thickness and erosion profile of the walls of such furnaces. As a result, manufacturers experience either an unexpected leakage of molten material through the furnace wall or conservatively shut down the furnace for re-build to reduce the likelihood of any potential leakage, based on the manufacturer's experience of the expected lifetime of the furnace. The lifetime of a furnace is affected by a number of factors, including the operational age, the average temperature of operation, the heating and cooling temperature rates, the range of temperatures of operation, the number of cycles of operation, and the type and quality of the refractory material as well as the load and type of the molten material used in the furnace. Each of these factors is subject to uncertainties that make it difficult to create accurate estimates of the expected lifetime of a furnace. Moreover, the flow of molten material, such as molten glass, at high temperatures erodes and degrades the inner surface of the refractory material and creates a high risk for molten glass leakage through the refractory wall. A major leak of molten glass through the gaps and cracks in the furnace walls may require at least 30 days of production disruption before the furnace can be restored to operating mode because it needs to be cooled down, repaired, and fired up again. Furthermore, a leak of molten glass may cause significant damage to the equipment around the furnace and, most importantly, put at risk the health and life of workers. For these reasons, in most cases furnace overhauls are conducted at a substantially earlier time than needed. This leads to significant costs for manufacturers in terms of their initial investment and the reduced production capacity over the operational life of the furnace.

Another important issue is that the material used to build the refractory chamber of the furnace may have internal flaws not visible by surface inspection. This could translate into a shorter life of the furnace and pose serious risks during furnace operation. Accordingly, on the one hand the refractory material manufacturer would like to have a means to evaluate the material during manufacture to be able to qualify the material for furnace construction following quality standards to deliver material with no flaws. On the other hand, the customer purchasing the refractory material would like to have a means for performing internal inspections of such material before constructing a furnace.

Previous efforts have been made to use microwave signals to measure the thickness of materials such as furnace walls, as described in U.S. Pat. No. 6,198,293 to Woskov et al. and U.S. Pat. App. No. 20130144554 by Walton et al. However, these efforts have faced certain challenges and limitations. In particular, attempts made to determine furnace wall thickness on hot furnaces have been generally unsuccessful because of the large signal losses involved in evaluating the inner surface of refractory materials, especially at relatively high frequency bands. Likewise, at relatively low frequency bands signals still experience losses and are limited in terms of the bandwidth and resolution required by existing systems. Moreover, in placing system components close to the surface of the refractory material to be evaluated, spurious signal reflections make it difficult to isolate the reflected signal of interest, thus further complicating the evaluation of the status of either the inner surface or the interior of such materials. A major challenge is that furnace walls become more electrically conductive as temperature increases. Therefore, signals going through a hot furnace wall experience significant losses making the detection of these signals very challenging.

Thus, there remains a need in the art for systems and methods capable of remotely evaluating the status of such refractory materials, through measurements of propagating electromagnetic waves, that avoid the problems of prior art systems and methods.

SUMMARY OF THE INVENTION

An improved system and method to evaluate the status of a material is disclosed herein. One or more aspects of exemplary embodiments provide advantages while avoiding disadvantages of the prior art. The system and method are operative to identify flaws and measure the erosion profile and thickness of different materials, including refractory materials, using electromagnetic waves. The system is designed to reduce a plurality of reflections associated with the propagation of electromagnetic waves launched into the material under evaluation, by a sufficient extent so as to enable detection of electromagnetic waves of interest reflected from remote discontinuities of the material. Furthermore, the system and method utilize a configuration and signal processing techniques that reduce clutter and enable the isolation of electromagnetic waves of interest. Moreover, the launcher used in the system is impedance matched to the material under evaluation, and the feeding mechanism is designed to mitigate multiple reflection effects to further suppress clutter.

The system launches electromagnetic waves into a near surface of a material to be evaluated. The electromagnetic waves penetrate the material and reflect from discontinuities inside and from both the near and a remote surface of the material. The reflected electromagnetic waves are received by a computer-based processor and timed, using as reference the wave reflected from the near surface of the material. The computer-based processor determines the delay in time between the reference wave and other reflected electromagnetic waves, which include undesired clutter. Where the magnitude of the clutter is below the magnitude of the electromagnetic waves reflected from remote discontinuities of the material, the computer-based processor identifies a peak level of magnitude associated with these discontinuities and determines the distance from such discontinuities to the near surface of the material associated with the reference wave. One or more evaluations over an area of the material provides the thickness of the material and the location of flaws inside the material at each evaluation to create an erosion profile of the remote surface of the material.

The system also includes an electromagnetic wave launcher designed and adapted to reduce a plurality of reflections that significantly contribute to the clutter received by the computer-based processor. The launcher provides levels of clutter reduction by a sufficient extent so as to enable detection of electromagnetic waves of interest that otherwise might not be possible. The launcher may be used in evaluation of the refractory walls of hot furnaces to create an erosion profile of the surface of the inner walls in an operational furnace.

The method to evaluate the status and measure the erosion profile and thickness of different materials includes the step of setting up the electromagnetic wave launcher conformally contiguous to the near, outer surface of the material under evaluation. The method further includes the steps of launching electromagnetic waves into the material and measuring, over a frequency band, the amplitude and the phase of waves reflecting from discontinuities from said material. The method also includes transforming measured data to time domain, calibrating the data to distance domain, and identifying data associated with reflected electromagnetic waves of interest; in particular, waves reflected from the inner, remote surface of the material under evaluation to determine the thickness of such material.

By significantly reducing the level of clutter caused by reflections and ringing of propagating electromagnetic waves, as compared to standard techniques, and by determining the location of remote discontinuities from the material under evaluation, the system and method are able to identify flaws and measure the erosion profile of the remote surface of such material.

BRIEF DESCRIPTION OF THE DRAWINGS

The numerous advantages of the present invention may be better understood by those skilled in the art by reference to the accompanying drawings in which.

DETAILED DESCRIPTION OF THE INVENTION

The following description is of a particular embodiment of the invention, set out to enable one to practice an implementation of the invention, and is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Figure 1:
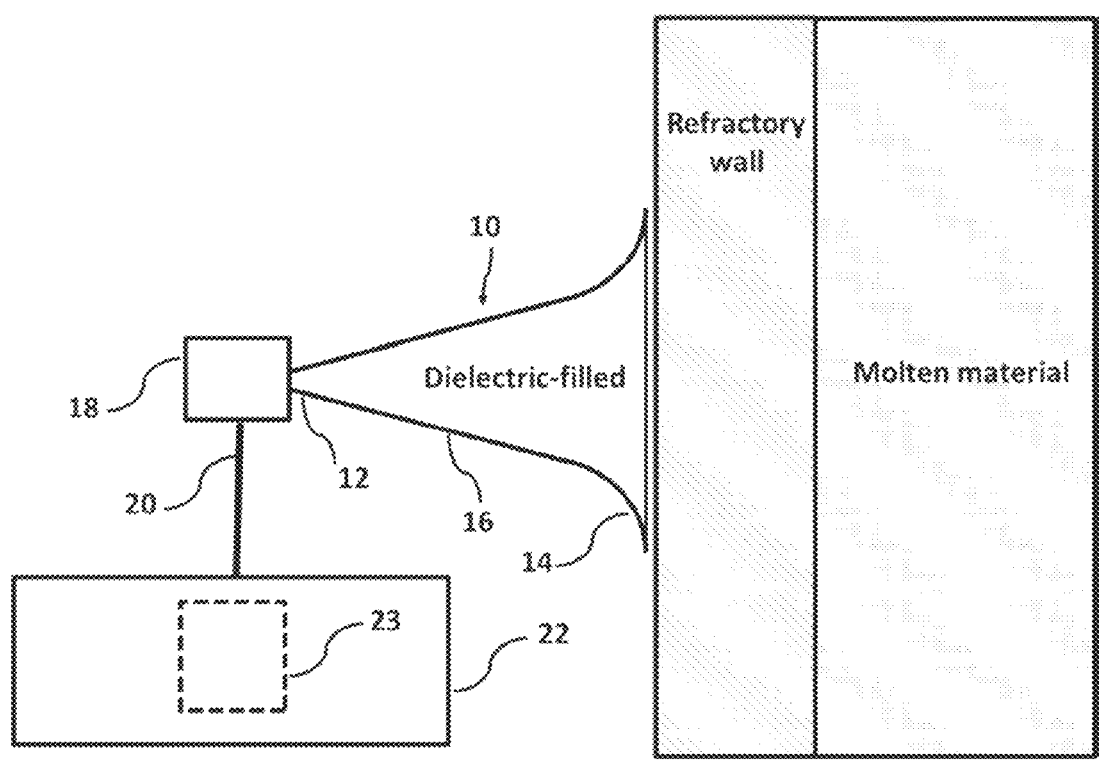
FIG. 1 shows a schematic view of an exemplary embodiment of a system using a rolled-edge electromagnetic wave launcher.

In accordance with certain aspects of an embodiment of the invention, a material evaluation system is shown in FIG. 1. The system is configured to evaluate a status of a refractory material used as a furnace wall. Thus, the refractory material has an outer surface and an inner surface opposite the outer surface. The inner surface of the refractory material is contiguous to (i.e., in contact with) a molten material, such as glass, plastic or steel or any other material contained within the furnace. An electromagnetic (EM) wave launcher 10, comprising a feeding end 12, a launching end 14, and an elongated section 16 in between and adjoining feeding end 12 and launching end 14, is disposed contiguous to an area of the outer surface of the refractory material to be evaluated. EM wave launcher 10 is designed to operate at a frequency band large enough to cover the operational frequency band of the system. Specifically, and as discussed in greater detail below, the dimensions of the rectangular cross section (width and height) at the launching end of EM wave launcher 10, the length of the launcher (or alternatively the width and height flare angles and the length), and the dielectric properties of the material occupying the internal volume of EM wave launcher 10 are all selected to cause EM wave launcher 10 to operate at a sufficiently large frequency band to cover the operational frequency band of the system, and with regard to certain aspects of an embodiment of the invention, in the frequency band from 0.5 GHz to 10 GHz. Likewise, EM wave launcher 10 is designed to tolerate the required temperature range of the near, outer surface of a furnace wall. More particularly, the material that is used to form EM wave launcher 10 is selected to allow EM wave launcher 10 to withstand such high temperatures (the area of the launcher exposed to the highest temperature being the area placed contiguous to the furnace outer surface). For example, the conductive material on the sides and on the rolled edges of the launcher is selected so as to have a melting temperature point larger (including some appropriate safety margin as may be selected by those skilled in the art) than the temperature of the furnace outer surface. Likewise, with regard to the dielectric material occupying the internal volume of the launcher as discussed in greater detail below, typical ceramic-type materials withstand temperatures much higher than the maximum expected temperature of the furnace outer surface. With regard to certain aspects of an embodiment of the invention, the dielectric substrate material also has similar properties to those of the ceramic material, in terms of temperature of operation. Finally, in the case that a variable conductivity material is used (again as discussed in greater detail below), the protecting layers of adhesive provide temperature isolation to the variable conductivity material. Preferably, the selection of such materials will allow use of the EM wave launcher 10 against a surface having a temperature as high as 1600° F. for a few seconds, which is sufficient enough to take the necessary data for operation. However, for longer duration operation, such materials should be able to withstand an ambient temperature limit of approximately 700° F., with the surface reaching temperatures up to approximately 1000° F.

As used herein, "near" surface is also intended to refer to the outer surface of the material under evaluation that is contiguous to launching end 14 of EM wave launcher 10. Likewise, "remote" surface is also intended to refer to the inner surface of the material under evaluation opposite the near surface immediately adjacent launching end 14 of EM wave launcher 10. Thus, in the case of a furnace, the remote surface comprises the inner surface of the outer wall of the furnace, and the near surface comprises the outer surface of the outer wall of the furnace.

Feeding end 12 includes a feeding transition section 18 electrically connected to a radiofrequency (RF) transmission line, such as a coaxial cable 20. A computer-based processor 22 is also electrically connected to coaxial cable 20. Accordingly, coaxial cable 20 is electrically connected at a first end to computer-based processor 22, and at a second end to feeding transition section 18. Coaxial cable 20 is selected to have a physical length from computer-based processor 22 to feeding transition section 18, such that a propagation time of an EM wave propagating between first end and second end of coaxial cable 20 is larger than a propagation time of the EM wave from feeding transition section 18 to the remote inner surface of the refractory material under evaluation and back to the near, outer surface of the material. In other words, the propagation time of the EM wave propagating throughout the length of coaxial cable 20 is larger than the propagation time of the EM wave propagating throughout EM wave launcher 10 plus the propagation time of the EM wave propagating back and forth through the thickness of the refractory material.

Computer-based processor 22 comprises an RF subsystem 23, a signal processing subsystem, and executable computer code or software. RF subsystem 23 comprises a tunable signal source, such as a voltage controlled oscillator or a frequency synthesizer, preferably operable in a frequency band going somewhere from 0.25 GHz to 30 GHz; at least one directional coupler; a coherent detector; and at least one analog-to-digital converter. The signal processing subsystem comprises data storage and data processing algorithms. Referring again to FIG. 1, it is noted that components of computer-based processor 22 have not been shown as these components are not critical to the explanation of this embodiment. Those of ordinary skill in the art will realize that various arrangements of RF subsystem 23 components may be possible and additional components, such as filters, impedance matching networks, amplifiers, non-coherent detectors and other test instrumentation may be used as different ways to implement RF subsystem 23 functions of computer-based processor 22 as are known in the prior art.

Launching end 14 of EM wave launcher 10 is placed in physical contact with the refractory material to be evaluated. More specifically, launching end 14 is preferred to be physically conformal to the area of the near surface of the refractory material with which launching end 14 is in physical contact (i.e., is configured so as to minimize spacing between launching end 14 and the surface under examination). In other words, it is not desired to have any gap or clearance larger than 2 mm between the surface of launching end 14 and the area of the near surface of the refractory material with which launching end 14 is in physical contact.

Elongated section 16 of EM wave launcher 10 is preferably selected to have a physical length from feeding end 12 to launching end 14 such that a propagation time of an EM wave propagating from feeding end 12 to launching end 14 is larger than a propagation time of said EM wave propagating from the near, outer surface of the refractory material under evaluation to the remote, inner surface of the material. In other words, the propagation time of the EM wave propagating along the EM wave launcher 10 is preferred to be larger than the propagation time of the EM wave propagating through the thickness of the refractory material. Typical thickness values of refractory material of furnace walls range from 0.5 inches to 12 inches. Accordingly, depending on the target range of thickness measurements, the length of elongated section 16 of EM wave launcher 10 typically ranges somewhere from 2 inches to 15 inches.

Figure 2A:
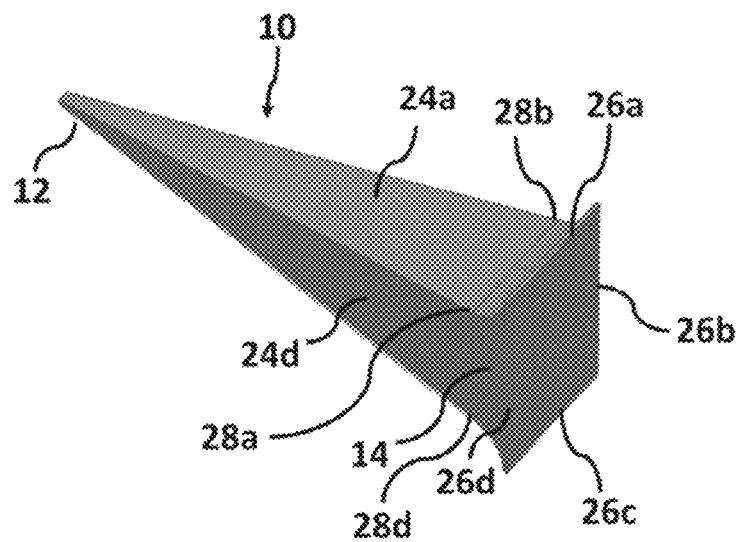
FIGS. 2A to 2D show various aspects of an electromagnetic wave launcher with two rolled edges in accordance with one embodiment.
Figure 2B:
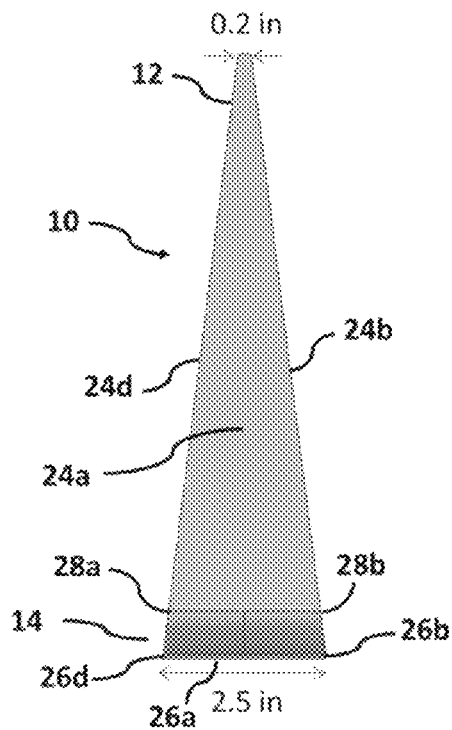
Figure 2C:
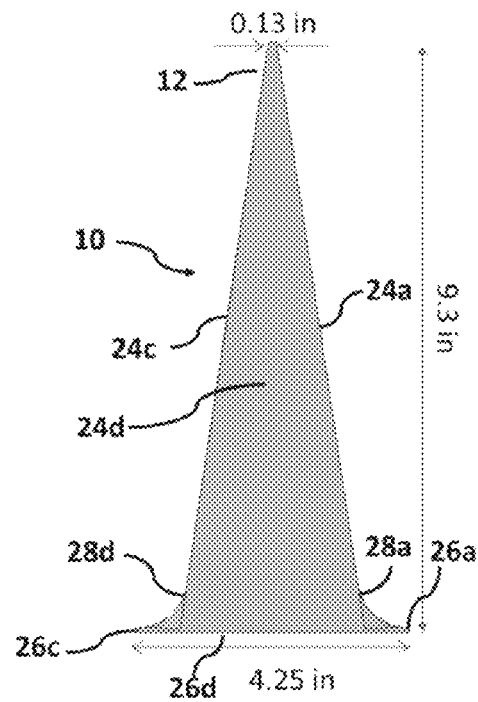

FIGS. 2A to 2D show various aspects of one version of EM wave launcher 10, used in FIG. 1. In this embodiment, FIG. 2A illustrates a perspective view of EM wave launcher 10, physically structured as a truncated, two-edge flared pyramid with a rectangular cross-section from feeding end 12 to launching end 16. FIGS. 2B and 2C show side views of EM wave launcher 10 having rectangular cross-section dimensions of 0.2 inches×0.13 inches at feeding end 12 and 2.5 inches×4.25 inches at launching end 14. Accordingly, four side plates 24a, 24b, 24c, and 24d form EM wave launcher 10. Each side plate 24a, 24b, 24c, and 24d is preferably made of a dielectric or conductive material. Typically, a conductive material having a thickness in the range of 0.01 inches and 0.25 inches, and more preferably between 0.05 inches and 0.1 inches is used. In the particular embodiment shown in FIG. 2D, a conductive material approximately 0.078-inches thick was used. Thus, more specifically, side plates 24a, 24b, 24c, and 24d of EM wave launcher 10 form a structure that surrounds, without fully enclosing, an internal volume of EM wave launcher 10. Side plates 24a, 24b, 24c, and 24d of EM wave launcher 10 do not surround the internal volume at feeding end 12 and launching end 14 of EM wave launcher 10.

Figure 2D:
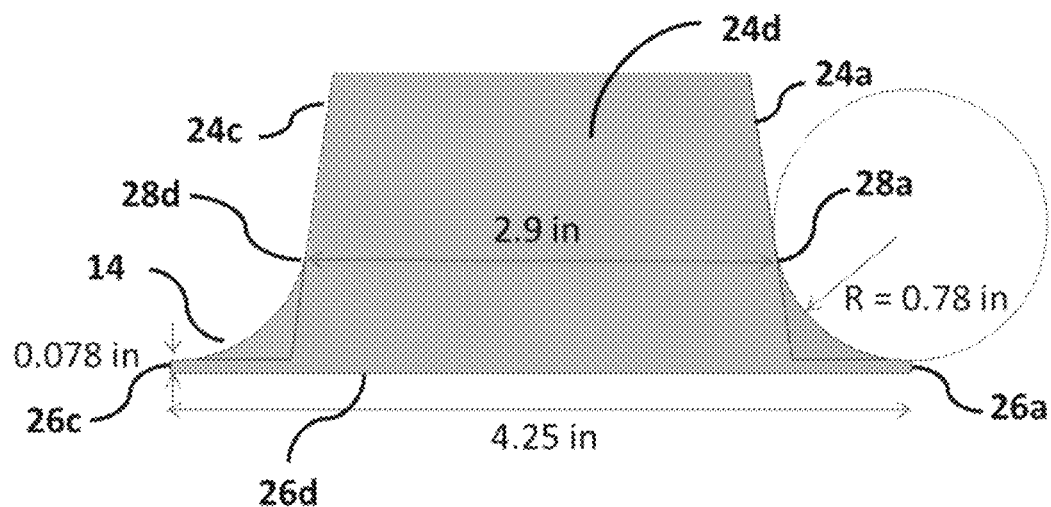

Referring again to FIG. 2A, at any cross-sectional view, four edges 26a, 26b, 26c, and 26d form the rectangular cross section of EM wave launcher 10. The dimensions of such rectangular cross-section of EM wave launcher 10 linearly increase from feeding end 12 to transition points 28a, 28b, 28c and 28d, which are located along elongated section 16 in between feeding end 12 and launching end 14. Accordingly, the shape of EM wave launcher 10, from feeding end 10 to transition points 28a, 28b, 28c, and 28d, corresponds to the shape of a regular rectangular cross-section pyramid. However, from transition points 28a, 28b, 28c, and 28d to launching end 14, the dimension of each end of opposite edges 26a and 26c of the rectangular cross-section of EM wave launcher 10 increases following a curve described by a circular function with a 0.78 inches radius of curvature, as shown in FIG. 2D. More specifically, the structure of EM wave launcher 10 corresponds to the structure of a truncated rectangular cross-section pyramid having two elliptically-flared or elliptically-rolled opposite edges. Typical values of a thickness of launching end 14 may range between 0 and 0.25 inches. In this particular embodiment, launching end 14 has a thickness of 0.078 inches. Likewise, the rolling of edges 26a and 26c starts at a point where a separation between transition points 28a and 28b or equivalently between transition points 28c and 28d is 2.9 inches. Accordingly, transition points 28a, 28b, 28c, and 28d are located approximately 0.63 inches from launching end 14.

Furthermore, EM wave launcher 10 is physically configured to have an impedance at launching end 14 that substantially matches an impedance of the near surface of the refractory material. The internal volume of EM wave launcher 10 may be at least partially filled with a solid ceramic filling material having an impedance that substantially matches a predetermined impedance of the refractory material under the normal operating conditions of the furnace. This predetermination may be obtained by measuring the dielectric properties of the refractory material at various temperatures using methods well known in the prior art. Alternatively, the manufacturer of the refractory material may provide data about the dielectric properties of the material at different temperatures. These data can be used to determine the impedance of the material. The impedance of the refractory material is primarily determined by both a relative dielectric permittivity of the material and a tangent loss of the material. Typically, the relative dielectric permittivity may range from 1 to 25 depending on the specific type of material and temperature of the material. Thus, the internal volume of EM wave launcher 10 may be partially or completely filled with a dielectric filling material of similar relative dielectric permittivity to that of the refractory material to substantially match the impedance of the refractory material.

The filling material used to fill the internal volume of EM wave launcher 10 may be air, liquid or solid. Preferably the filling material is a mixture of solid powder or granulated material in which the maximum dimension of each grain is desired to be no larger than ten percent of a wavelength of an EM wave propagating in EM wave launcher 10 at the lowest frequency of operation. More preferably, the filling material is a solid ceramic piece of material or the like adapted to fit into the internal volume of EM wave launcher 10. Alternatively, the internal volume of EM wave launcher 10 may be layered, from feeding end 12 to launching end 14, so that each layer is filled with a filling material that has a slightly different dielectric permittivity to the dielectric permittivity of the filling material of any adjacent layer to structure multiple layers of different dielectric permittivity in an arrangement that gradually adjust an impedance from feeding end 12 to the impedance of the refractory material to be evaluated at launching end 14. Whenever necessary a lid or cap may be placed at feeding end 12 and launching end 14 to prevent the filling material from exiting the internal volume of EM wave launcher 10 during manipulation or operation of EM wave launcher 10. Those skilled in the art realize that a cap placed at launching end 14 must be made of a material having similar dielectric characteristics as those as the filling material to prevent a substantial discontinuity to an EM wave propagating through said cap. Likewise, a cap placed at feeding end 12 must be made of a material according to a specific design of feeding transition section 18.

Figure 3:
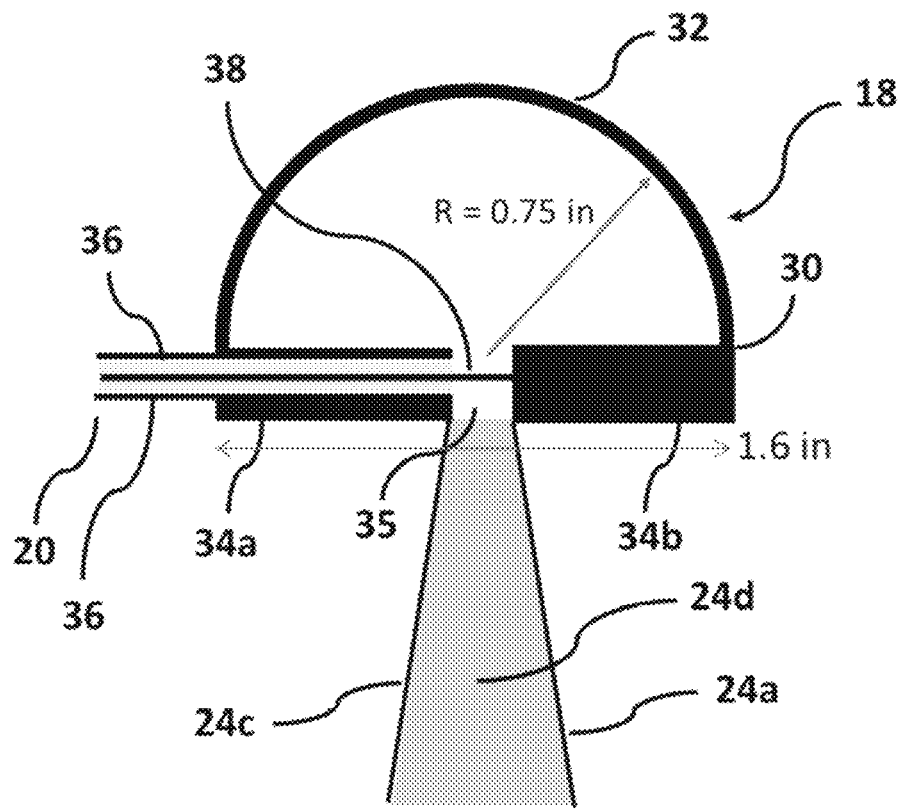
FIG. 3 shows a design of a feeding transitioning section.

FIG. 3 shows a design of a feeding transitioning section 18 using a cap 30 formed by a shell of a conductive material having a thickness of approximately 0.1 inches. Cap 30 forms an air-filled cavity surrounded by the shell, having a semicircular cross-section in a first dimension, and a rectangular cross-section in a second dimension normal to said first dimension. In this embodiment, the semicircular cross-section is defined by a semicircular section 32, having an internal radius of approximately 0.75 inches, and a linear section of approximately 1.6 inches, comprising a first section 34a and a second section 34b of substantially the same dimensions, separated by a gap 35, whereas said rectangular cross-section is defined by said linear section, defining a width of approximately 1.6 inches, and another linear section, defining a length of approximately 1.3 inches (not shown in FIG. 3).

Cap 30 has a first circular opening at one side of semicircular section 32 large enough to just allow coaxial cable 20 to enter inside of the cavity. Outer conductor 36 of coaxial cable 20 is electrically connected to both semicircular section 32 of cap 30 and conductive side plate 24a of EM wave launcher 10 at feeding end 12. A pin or probe 38 is formed by extending a center conductor of coaxial cable 20 beyond outer conductor 36 of coaxial cable 20 inside of the cavity; in this case the pin length is approximately 0.1 inches. Likewise, gap 35 of cap 30 defines a second opening that separates linear section 34a from linear section 34b. The dimensions of gap 35 are large enough just to allow the tip of the truncated end of EM wave launcher 10, that is closer to feeding end 12, to fit into the cavity. In this embodiment, side plates 24a and 24c of EM wave launcher 10 are made of conductive material. Accordingly, side plate 24a of EM wave launcher 10 is electrically connected to second section 34b, and side plate 24c of EM wave launcher 10 is electrically connected to first section 34a. Also, outer conductor 36 of coaxial cable 20 is electrically connected to the first section 34a. Additionally, pin 38 is electrically connected to the second section 34b. In this way, EM wave launcher 10 may be excited by pin 38 of coaxial cable 20 in a cavity-backed feeding pin configuration. Typically, pin 38 is located at a distance from the cap equal to a quarter wavelength corresponding to a center frequency of the frequency band of the EM waves propagating along EM wave launcher 10.

Those skilled in the art will realize that semicircular section 32 may be shaped following different configurations, such as elliptical, planar or other smooth function. Likewise, one or more sections of cap 30 may be removed in certain configurations, and the cavity may be filled with dielectric material. Furthermore, the dimensions of linear sections 34a and 34b may be designed in combination with feeding end 12 of EM wave launcher 10 to reduce undesirable ringing effects.

Operation

In accordance with further aspects of an embodiment of the invention, the manner of using the material evaluation system of FIG. 1 is based on the fundamentals of EM wave propagation. Computer-based processor 22 controls the tunable RF signal source, operating in a frequency band that properly penetrates the refractory material with low enough loss, preferably somewhere between 0.25 GHz and 30 GHz, and more preferably operating in a frequency range somewhere between 0.25 GHz and 10 GHz. The RF signal source is carried by coaxial cable 20 to feeding transition section 18 in order to excite at least one propagation mode within EM wave launcher 10 such that a number of EM waves are able to propagate from feeding end 12 to launching end 14 at the frequency range of interest. The bandwidth of the EM waves propagating in EM wave launcher 10 is typically selected to be at least 2 GHz to permit the resolution required by the user.

Upon reaching EM wave launcher 10, the RF signal source from computer-based processor 22 will experience an initial discontinuity at feeding transition section 18 resulting from adapting EM fields of the RF signal source propagating along coaxial cable 20 to EM fields of propagating modes excited inside EM launcher 10. This initial discontinuity causes a part of the RF signal source to reflect back to computer processor 22.

Additionally, once EM waves propagating along EM wave launcher 10 reach the near, outer surface of the refractory material, a first part of the EM waves will penetrate through the near, outer surface of the material and propagate inside the material until reaching the remote, inner surface of the material. A second part of the EM waves will reflect back, from the near, outer surface of the refractory material, to EM wave launcher 10 and a part of the reflected EM waves will propagate until reaching computer processor 22. Upon the first part of the EM waves reaching the remote, inner surface of the refractory material, a third part of the EM waves will penetrate through and propagate inside the molten material contained within the furnace. A fourth part of the EM waves will reflect back, from the remote, inner surface of the refractory material, to EM wave launcher 10 and a part of the reflected EM waves will propagate until reaching computer processor 22. The second part of the EM waves reflect as a result of the waves propagating through a media discontinuity between internal volume of EM wave launcher 10 at launching end 14 and the refractory material. Likewise, the fourth part of the EM waves reflect as a result of the waves propagating through a media discontinuity between the refractory material and the molten material.

Furthermore, EM waves propagating through the refractory material may experience discontinuities resulting from a presence of an inhomogeneous region or a flaw inside the refractory material. As such, a part of the EM waves will reflect back, from the flaw inside the refractory material, to EM wave launcher 10 and a part of the reflected EM waves will propagate until reaching computer processor 22.

Even further, EM waves propagating along EM wave launcher 10 will experience an additional edge discontinuity at launching end 14. More specifically, the edge discontinuity will occur at edges 26a, 26b, 26c, and 26d corresponding to launching end 14, as shown in FIG. 2A, as a result of the waves propagating through a media discontinuity between the internal volume of EM wave launcher 10 at launching end 14 and media surrounding the edges, such as the near, outer surface of the refractory material, and the medium surrounding EM wave launcher 10, such as air. Accordingly, part of the EM waves will reflect back from the edges to EM wave launcher 10 and a part of the reflected EM waves will propagate until reaching computer processor 22.

Moreover, the EM waves reflected from edges 26a, 26b, 26c, and 26d corresponding to launching end 14 may reach one or more of the other edges multiple times to create an undesirable "ringing" or "reverberation" effect due to multiple edge reflections of the EM waves. Eventually, part of the multiple reflected EM waves will reach computer processor 22.

Likewise, any reflected wave within EM wave launcher 10 within the refractory material or between feeding end 12 and computer processor 22 will be affected by any discontinuity at the near, outer surface of the refractory material, launching end 14, and feeding end 12. In other words, the effects of a discontinuity will affect propagating EM waves regardless of the direction of propagation of the EM waves, either from computer processor 22 to the remote, inner wall of the refractory material or from the remote, inner wall of the refractory material to computer processor 22. Accordingly, multiple EM wave reflections occur that may create ringing effects and adversely affect an ability of computer processor 22 to detect a reflected EM wave of interest. In other words, a number of spurious signals or undesired EM wave reflections are inherently present that may cause serious performance issues of the material evaluation system. A term commonly used to refer to the aggregated effects of such spurious signals or undesired EM wave reflections is "clutter."

In particular, a first EM wave of interest to evaluate the status of the refractory material is an initial reflected EM wave from the discontinuity between launching end 14 and the near, outer wall of the refractory material to establish a reference for determining the thickness of the refractory material or determining the location of a flaw inside said material. A second EM wave of interest is an initial reflected EM wave from the discontinuity between the remote, inner wall of the refractory material and the molten material within the furnace to determine the thickness of the refractory material. A third EM wave of interest is an initial reflected EM wave from a discontinuity of a flaw inside the refractory material to determine the location of the flaw.

Correspondingly, a number of different terms are major contributors to the overall clutter in the system. A first term corresponds to the reflected RF signal from feeding transition section 18 to computer-based processor 22. A second term corresponds to the multiple RF signal reflections or ringing between feeding transition section 18 and computer-based processor 22. A third term corresponds to the reflected EM wave from edges 26a, 26b, 26c, and 26d at launching end 14 to computer-based processor 22. A fourth term corresponds to the multiple edge reflections or ringing of EM waves from edges 26a, 26b, 26c, and 26d at launching end 14 to computer-based processor 22. A fifth term corresponds to the multiple reflections or ringing of EM waves between the near, outer wall of the refractory material and the remote, inner wall of the refractory material that reach computer-based processor 22. A sixth term corresponds to the multiple reflections or ringing of EM waves between a flaw inside the refractory material and the near, outer wall of the refractory material that reach computer-based processor 22. A seventh term corresponds to the multiple reflections or ringing of EM waves between a flaw inside the refractory material and the remote, inner wall of the refractory material that reach computer-based processor 22. An eighth term corresponds to the multiple reflections or ringing of EM waves between feeding end 12 and the near, outer wall of the refractory material that reach computer-based processor 22.

A ninth term corresponds to the multiple reflections or ringing of EM waves between feeding transition section 18 and feeding end 12 that reach computer-based processor 22.

In this embodiment, an RF signal or EM wave that is received by computer-based processor 22 goes through a coherent detector that provides voltages proportional to the in-phase (I) and quadrature-phase (Q) components of the received RF signal or EM wave relative to a reference version of the original RF signal source; thus permitting both amplitude and relative phase to be measured. The reference version of the original RF signal source is provided by a sample obtained by means of a directional coupler. Analog-to-digital converters output digital data proportional to the I voltage and the Q voltage outputs of the coherent detector. The digital data is then read, stored, and processed by computer-based processor 22. Optionally, computer-based processor 22 further adapts the processed data to display the results to the user. Computer-based processor 22 has executable computer code configured to measure reflected EM waves received to produce frequency domain data and transform the frequency domain data to time domain data. Furthermore, computer-based processor 22 calibrates the time domain data to distance domain data, identifies a peak in the distance domain profile associated with an EM wave of interest reflected from the refractory material, and determines a distance traveled by the EM wave of interest.

Thus, computer-based processor 22 is capable of determining a relative time delay between a received RF signal or EM wave and the original RF signal source. The time domain data can be used to determine the relative time of arrival of each EM wave of interest and the clutter terms. Of particular importance is that any EM wave of interest will be received during an interval of time between the arrival of the first EM wave of interest, used as a reference, and the arrival of the second EM wave of interest. In other words, any information of the status of the refractory material will arrive to computer-based processor 22 during this interval of time. Accordingly, the only clutter terms that may arrive during this interval of time at computer-based processor are those corresponding to the second, third, fourth, sixth, eighth, and ninth clutter terms.

Furthermore, by selecting the length of coaxial cable 20 such that the propagation time of an EM wave propagating throughout the length of coaxial cable 20 is larger than the propagation time of the EM wave propagating throughout EM wave launcher 10 plus the propagation time of the EM wave propagating back and forth through the thickness of the refractory material, the multiple reflections corresponding to the second clutter term will arrive at computer-based processor 22 later than any EM wave of interest. Likewise, by selecting the length of elongated section 16 of EM wave launcher 10 such that the propagation time of an EM wave propagating along EM wave launcher 10 is larger than the propagation time of the EM wave propagating through the thickness of the refractory material, the multiple reflections corresponding to the eighth clutter term will arrive at computer-based processor 22 later than any EM wave of interest.

The ringing effects produced by the sixth clutter term, i.e., the ringing of EM waves between a flaw inside the refractory material and the near, outer wall of the refractory material that reach computer-based processor 22, will arrive at computer-based processor 22 at the same interval time as the EM waves of interest only if the flaw is located closer to the near, outer wall of the refractory material than to the remote, inner wall of the material. However, this effect will be noticeable only when a flaw is present at a distance from the near, outer wall of the material that is smaller than half of the thickness of the material. Those skilled in the art will realize that measurements at multiple frequencies and known signal processing techniques may allow determining when this situation occurs.

As shown in FIG. 3, the use of a cavity-backed feeding transitioning in this embodiment may reduce the effects of the ninth clutter term, i.e., the ringing of EM waves between feeding transition section 18 and feeding end 12 that may reach computer-based processor 22 during the same time interval as an EM wave of interest. Because of the inherent wideband requirement of EM wave launcher 10, the critical quarter-wavelength distance is difficult to maintain over the whole frequency band of operation. Accordingly, the ringing effects may partly, although still significantly, be removed.

Therefore, the most relevant and at the same time the most difficult clutter terms to remove from the system are those related to edges 26a, 26b, 26c, and 26d at launching end 14. These are the third and fourth clutter terms as described above.

Figure 4:
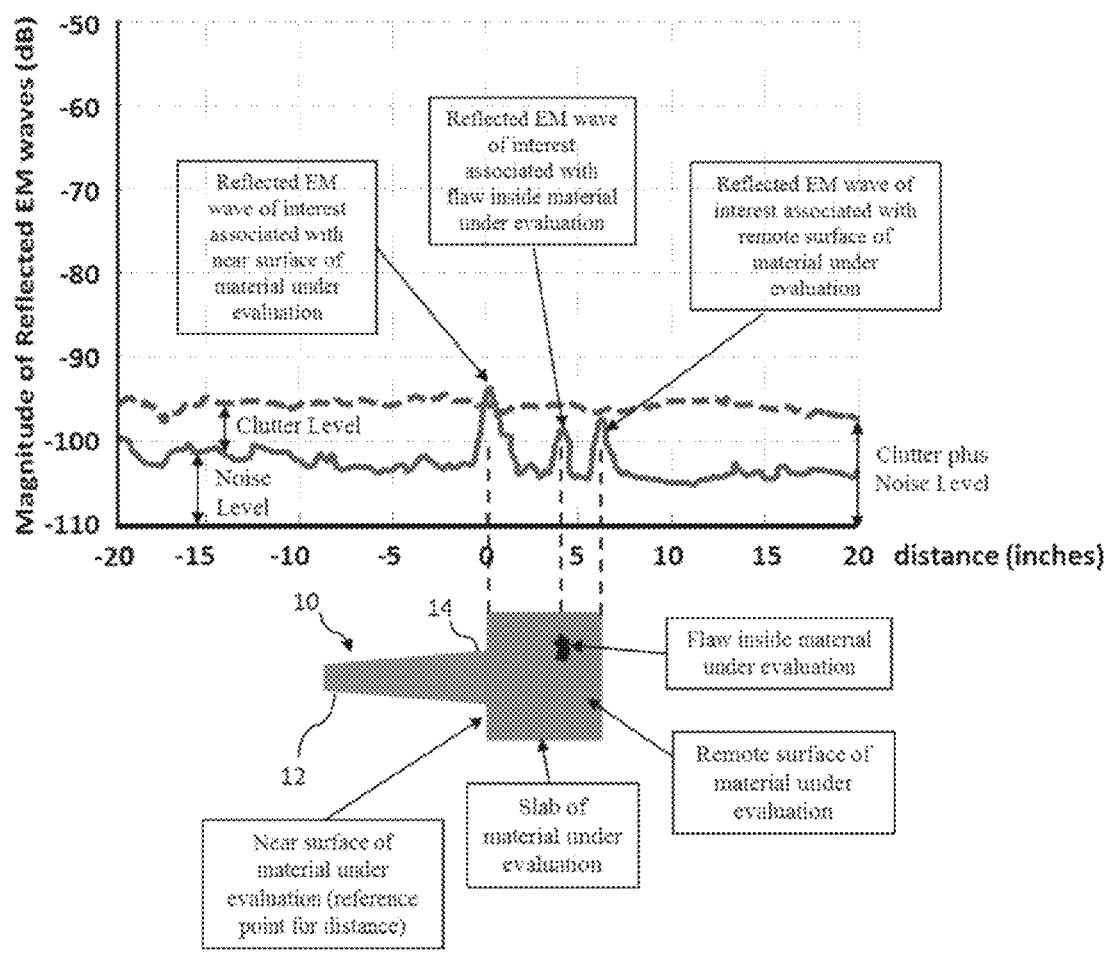
FIG. 4 shows a plot of the magnitude of the noise, clutter, and reflected electromagnetic waves of interest in accordance with a hypothetical scenario.

The computer executable code of computer-based processor 22 allows calibration of the time domain data to a distance domain data based upon a known velocity of an EM wave travelling along coaxial cable 20 and EM wave launcher 10 and through the refractory material under evaluation. Also, the reference or zero distance value corresponds to the transition between launching end 14 of EM wave launcher 14 and the near, outer surface of the refractory material. FIG. 4 shows a plot of the magnitude of the received EM waves at computer-based processor 22 as a function of distance. This represents a possible scenario for the system shown in FIG. 1, wherein a flaw within the refractory material is present. The effect of the clutter terms in determining the EM waves of interest at computer-based processor 22 may be noticed. The solid line curve represents the magnitude of the EM waves of interest plus the system noise. The dashed line curve represents the magnitude of the clutter plus the system noise. Note also that the distance interval of interest is only the distance corresponding to the thickness of the refractory material, in this case approximately 6 inches. Where the magnitude of the clutter plus noise is about the same or larger than the magnitude of the EM waves of interest associated with both the flaw and the thickness of the refractory material, as shown in FIG. 4, those EM waves of interest cannot be detected by computer-based processor 22. Thus, neither the EM wave of interest associated with the flaw of the refractory material, showed approximately at a distance of 4 inches in FIG. 4, nor the EM wave of interest associated with the remote, inner wall of said material, showed approximately at a distance of 6 inches, can be detected due to the clutter effects. Accordingly, the thickness of the refractory material cannot be determined. In this case, only the magnitude of the EM wave of interest associated with the near, outer surface of the refractory material can be determined because it is above the magnitude of the clutter plus noise. However, determining the magnitude of only the EM wave of interest associated with the near, outer surface of the material is not very useful.

Hence, it is of utmost importance to reduce the magnitude of the clutter plus noise to a level below the magnitude of the EM waves of interest associated with the flaw or the thickness of the refractory material to be able to determine the status of the material. Typically, in most applications involving the evaluation of a refractory material, the clutter is so large that a material evaluation system becomes unreliable and, in general, unable to determine the status of the material. In addition, known techniques such as those based on subtraction of measurements of reflected EM waves taken at different locations on the surface of the furnace wall are ineffective to reduce the clutter. The reason for the ineffectiveness of the techniques is the variability of the clutter component associated with each of the measurements, caused by variations of the surface temperature, tangent loss, and set up of EM wave launcher 10 and the surface of the furnace wall, from measurement to measurement.

Figure 5:
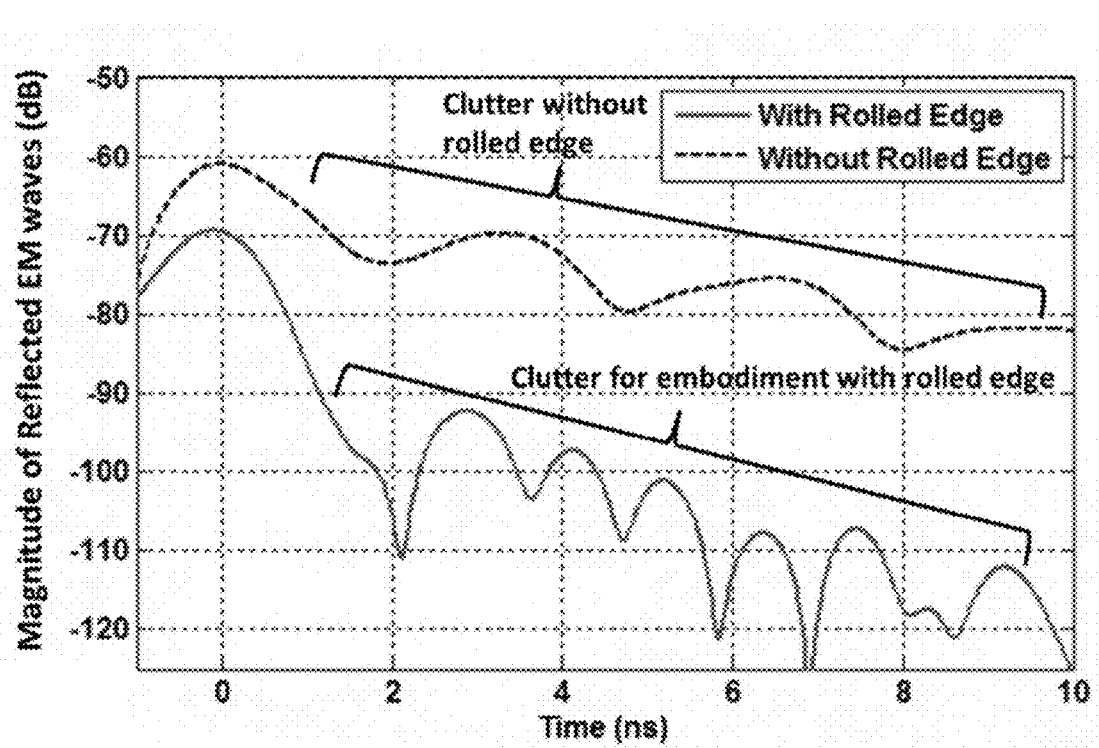
FIG. 5 shows a plot of the magnitude of the noise, clutter, and reflected electromagnetic waves of interest using a launcher with and without rolled edges.

FIGS. 1 and 2 show a design of EM wave launcher 10 that significantly reduces the clutter terms related to edges 26a, 26b, 26c, and 26d at launching end 14. As previously indicated, the clutter terms related to edges 26a, 26b, 26c, and 26d at launching end 14 are the most relevant and at the same time the most challenging clutter terms to suppress from the system. FIG. 5 shows actual measurement data of a 10-inches thick refractory material installed on an operating furnace. In this case, the thickness of the refractory wall was selected to be free of flaws and be so thick that there are no reflected EM waves from flaws and the reflected EM waves from the remote, inner surface of the furnace wall are so attenuated that they do not reach computer-based processor 22. Thus, FIG. 5 shows only results of clutter plus noise measurements for an EM wave launcher 10 with rolled edges and a substantially similar EM wave launcher 10 with no rolled edges. A solid line curve represents the magnitude of clutter plus noise of the processed time domain data using an EM wave launcher 10 with rolled edges, as described above. The dashed line curve represents the magnitude of clutter plus noise where a substantially similar EM wave launcher 10 without rolled edges is used. As seen in FIG. 4, an effect of using an EM wave launcher with rolled edges is a reduction in clutter plus noise of around 20 to over 30 dB in a region where the reflected EM wave of interest associated with the near, outer surface of the furnace wall would be expected to appear, such as the region where time is larger than 1 nanosecond.

Another effect of using an EM wave launcher with rolled edges is a reduction in clutter plus noise of as much as 10 dB for the reflected EM wave of interest associated with the near, outer surface of the furnace wall. Also, because the system noise is substantially similar in both cases, when using EM wave launcher 10 with and without rolled edges, the reductions in clutter plus noise levels observed in FIG. 5 correspond primarily to reductions in clutter levels.

With regard to FIG. 1, in which a single EM wave launcher 10 is used, such a system is commonly referred to as a mono-static configuration. Optionally, an additional EM wave launcher 10 may be added to only receive reflected EM waves. In such configuration, commonly known as a bi-static configuration, a first "active" EM wave launcher 10 will be used to launch the EM waves into the material under evaluation as shown in FIG. 1. A second "passive" EM wave launcher 10 is placed next to the first EM wave launcher 10. The second EM wave launcher 10 will only receive reflected EM waves. Thus, the reflected EM waves return to computer-based processor 22 using a different path from the path used by the launched EM waves. This provides an inherent separation between launched and received EM waves. Unlike FIG. 1, this bi-static configuration does not require an additional component, such as a directional coupler, to separate transmitted and received EM waves coming from and going to computer-based processor 22 to perform a coherent detection of the reflected EM waves.

Preferably, in a bi-static configuration, a center point of an imaginary plane containing launching end 14 of the first EM wave launcher 10 is placed as close as possible to a corresponding center point of a plane containing launching end 14 of the second EM wave launcher 10, having both launching ends conformally placed in contact with the near, outer surface of the refractory material. One reason for a preferred minimum separation between EM wave launchers in this configuration is that the distance traveled by the reflected EM waves is shorter, which results in less losses. A second reason is that the second EM wave launcher will be able to receive more reflected EM waves, especially those EM waves reflected at angles near 180 degrees with respect to the launched EM waves. Furthermore, to receive the reflected EM waves having a substantially same electric field polarization as an electric field polarization of the launched EM waves, in certain situations, an orientation of the first EM wave launcher 10 with respect to the second EM wave launcher 10 may be selected to have edges 24a, 24b, 24c, and 24d at launching end 14 of the first EM wave launcher 10 be substantially parallel to edges 24a, 24b, 24c, and 24d at launching end 14 of the second EM wave launcher 10. Those skilled in the art will recognize that a relative orientation of the first EM wave launcher 10 with respect to the second EM wave launcher 10 may need to be adjusted to receive the reflected EM waves having a substantially desired electric field polarization—such as co-polarized, cross-polarized, or any combination thereof—as compared to an electric field polarization of the launched EM waves. Furthermore, the second EM wave launcher is not required to be identical or similar to the first EM wave launcher.

With regard to still further aspects of the invention, where transverse electric and magnetic (TEM) waves are exclusively used, EM wave launcher 10 may be configured to have only two opposite side plates made of conductive material. In other words, in a first configuration only side plates 24a and 24c are made using a conductive material. In a second configuration, only side plates 24b and 24d are made using a conductive material. The preferred thickness dimensions for these two different configurations are the same as for the configuration having four conductive side plates, as shown in FIG. 2. Thus, more specifically, a first group of two opposite side plates of EM wave launcher 10 are made of conductive material, and a second group of two opposite side plates may be removed, be made of a dielectric or other material as known in the prior art, or simply be replaced by opposite surfaces of a solid filling dielectric material such as ceramic.

Further, EM wave launcher 10 may alternatively be provided at least two opposite side plates in which a material having a variable conductivity is disposed, instead of being made using a conductive material. Those skilled in the art will realize that one or more coating applications of a conductive material applied to a dielectric material filling the internal volume of EM wave launcher 10 may be used to achieve a desired profile of variable conductivity along the side plates. Alternatively, a film, uniform in thickness and having a variable conductivity may be disposed between feeding end 12 and launching end 14. More specifically, the variable conductivity material may be disposed on at least side plates 24a and 24c or at least side plates 24b and 24d. In this alternative embodiment, the internal volume of EM wave launcher 10 is filled with a solid dielectric, preferably ceramic. A variable conductive film is disposed on two opposite side surfaces of the dielectric, going from feeding end 12 to launching end 14, to form side plates 24a and 24c or 24b and 24d of EM wave launcher 10. In this configuration, a first end of the variable conductivity material is disposed closer to feeding end 12, and a second end of the variable conductivity material is disposed closer to launching end 14. Thus, electromagnetic waves propagate in EM wave launcher 10 within a region partly surrounded by the variable conductivity material, wherein the conductivity varies as a function of the distance from a point on the variable conductivity material to launching end 14. Alternatively, multiple sections of conductive films, each having a different conductivity, may be arranged sequentially from lower to higher conductivity to create an increasing conductivity profile as a function of distance from the first to the last of the sections. The thickness of each individual layer of conductive film is preferred to be in the range of between 0.001 inches and 0.1 inches.

Typically, a sheet resistance characterizes the degree of conductivity of a thin film layer of material of uniform thickness. A larger sheet resistance corresponds to a lower conductivity and vice versa. In the configuration described immediately above, the sheet resistance of the variable conductivity material increases following an exponential function from the first end of the variable conductivity material, closer to feeding end 12, to the second end of the variable conductivity material, closer to launching end 14.

In particular, the lowest value of sheet resistance of the variable conductivity material at the first end, closer to feeding end 12, is preferred to be below 1 Ohm per square. More preferably, the lowest value of sheet resistance is similar to the sheet resistance of a conductive material such as copper or silver. On the other hand, the highest value of sheet resistance of the variable conductivity material at the second end, closer to launching end 14, is preferred to be in a range somewhere between 50 Ohms per square and 1000 Ohms per square. More preferably, the lowest value of sheet resistance is similar to the sheet resistance of a dielectric material such as ceramic. In other words, the variable conductivity material behaves as a conductive material closer to feeding end 12 and gradually transitions to have the preferred maximum sheet resistance value as the variable conductivity material gets closer to launching end 14. This variable conductivity profile provides a significant reduction of reflections of EM waves from the edges at launching end 14. Accordingly, the variable conductivity profile provides a significant reduction of clutter resulting from EM waves reflecting from the edges at launching end 14.

The above described variable conductivity profile is substantially the same for each of at least two opposite side plates 24a and 24c or 24b and 24d of EM wave launcher 10. However, those skilled in the art will realize that different profiles in each side plate may be used. In general, the profile of the sheet resistance of the variable conductivity material may increase following a step, elliptical, exponential, or a smooth transitioning function, or any combination thereof, optimally designed to reduce the clutter, from the first end of the variable conductivity material, closer to feeding end 12, to the second end of the variable conductivity material, closer to launching end 14.

A critical issue in using a resistive film disposed relatively close to launching end 14 is that, under normal operating conditions, the refractory material may reach temperatures of several hundred degrees Fahrenheit at the near, outer surface of the furnace. Launching end 14 is in physical contact with the hot material. Hence, most likely, the film may be physically damaged unless protected. A conductive film may be sandwiched in between two layers of high-temperature adhesive to protect the film. This three-layer structure may be disposed on at least two opposite side surfaces of a dielectric material filling the internal volume of EM wave launcher 10, going from feeding end 12 to launching end 14, to form side plates 24a and 24c of EM wave launcher 10. In the present embodiment, the dielectric material and the three-layer structure was cured at a temperature of approximately 300 degrees Fahrenheit for a 2-hour period. Preferably, the film and each of the layers of adhesive has a thickness ranging somewhere between 0.001 inches and 0.01 inches. More preferably, the layers of adhesive have similar electrical properties as the electrical properties of the dielectric material. Furthermore, high-temperature ceramic cement or other equivalent material may be placed on top of the three-layer structure for increased protection. In this manner, a compact packaging is provided to not only protect the film from physical damage due to the high temperatures experienced by launching end 14 and from manipulation during set up and operation of EM wave launcher 10, but also to hold the film in place during operation. Those skilled in the art will realize that various types of adhesives and cement materials commercially available may be used, typically having a curing time between one hour and three hours at temperatures ranging from 200 to 500 degrees Fahrenheit.

The effects of configuring EM wave launcher 10 using a variable conductivity material as described are so significant in reducing clutter terms related to the edges of the launching end 14 of EM wave launcher 10 that an embodiment using the variable conductivity material may not require flared or rolled edges at launching end 14. Thus, either a first configuration using an EM launcher with rolled edges or a second configuration using an EM wave launcher having at least two side plates with a variable conductivity material may be used to significantly reduce edge reflections in most applications. Of course, a third configuration combining both techniques to reduce edge reflections will provide further improvement to the material evaluation system.

Launching end 14 of EM launcher 10 may extend following a topology of the near, outer surface of the material to be evaluated. Alternatively, the rolled edges of launching end 14 of EM wave launcher 10 may follow a circular function or other function that smoothly extends away sufficiently enough from transition points 28a, 28b, 28c, and 28d so as to reduce the effects of edge reflections.

Optionally, the entire material evaluation system may be packaged into a single portable unit in which an operator triggers the launch of EM waves, over a frequency band, by activating a switch. More specifically, the entire material evaluation system may be enclosed in a single hand held unit. The unit may evaluate the status of the furnace wall at a single point and record the information in a built-in memory. Alternatively, the EM wave launcher along with a subset of components of the material evaluation system may be integrated into a single assembly to launch the EM waves and to only measure, record, and store the amplitude and phase of the EM waves coming into the EM wave launcher. Then the stored data may be transferred to computer-based processor 22 using a portable memory drive or by means of a flexible cable for evaluating the status, or ultimately determining the thickness, of the subject material under evaluation. Alternatively, the data may be transferred wirelessly in real time or at a convenient opportunity. Furthermore, the hand held unit may include data processing components and a display to show the thickness of the furnace wall and/or the distance from the outer, near surface of the refractory material to a discontinuity embedded in the material under evaluation. The portable unit may be designed to scan by hand an area of the furnace wall while taking measurements at multiple locations. Moreover, EM wave launcher 10 may be periodically used for one or more evaluations of said material under evaluation, or may be installed permanently and fixed onto the outer, near surface of the material under evaluation to continuously monitor the status of the material under evaluation. Alternatively, a region of the outer, near surface of the material under evaluation may be scanned, by moving the EM wave launcher, during operation, over and while maintaining physical contact with the outer, near surface of the material under evaluation.

The RF front-end of RF subsystem 23 of computer-based processor 22 may be integrated with feeding transition section 18 of EM wave launcher 10. In other words, coaxial cable 20 may be removed from the system as it is no longer required. In this situation, any multiple reflections between the RF front-end and feeding transition section 18 will arrive to computer-based processor 22 before any of the reflected EM waves of interest. Alternatively, coaxial cable 20 may be disposed following a predetermined physical route to produce maximum stability of the RF signal or the EM wave travelling in the cable. Furthermore, such stability may be accomplished by mechanically attaching the cable to a supporting structure, so as to minimize any movement of coaxial cable 20. Likewise, preventing coaxial cable 20 from following a route requiring the cable to bend beyond a certain angle from a straight-line routing may help in reducing the overall clutter in the system.

Those skilled in the art will recognize that EM wave launcher 10 may be implemented using multiple devices and materials in various configurations that include one or more of an antenna, a waveguide, a dielectric material, a conductive material, a material having a variable conductivity, a metamaterial, or any combination thereof configured in different geometrical arrangements.

Figure 6:
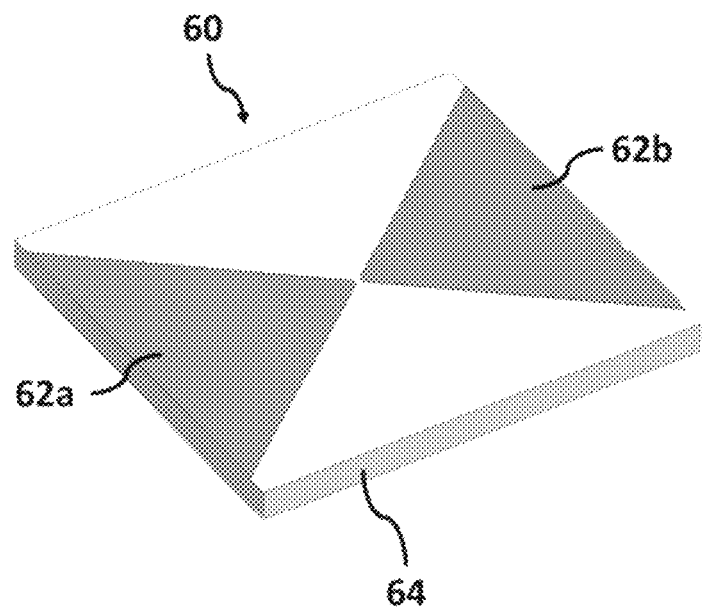
FIG. 6 shows a perspective view of a planar electromagnetic wave launcher in accordance with another embodiment.

In particular, FIG. 6 shows an optional configuration of a planar EM wave launcher 60 comprising a bow-tie antenna having a first layer 62a of conductive material and a second layer 62b of conductive material, wherein the edges of both of layers 62a and 62b are linearly tapered to have a triangular shape and are disposed on a top surface of dielectric substrate 64. EM wave launcher 60 is typically fed by a balanced-to-unbalanced device, referred to as a "balun," that adapts an impedance of an unbalanced transmission line, such as a coaxial cable, to an input impedance of the bow-tie antenna. In this configuration, the input impedance of the bow-tie antenna is substantially matched to the impedance of the near, outer surface of the refractory material. Substrate 64 has an underside surface, with a layer of conductive material disposed over all of the underside surface to form a ground plane, and two openings to allow the balun to feed the bow-tie antenna. Typically, these openings are made through the smallest dimension or thickness of substrate 64 and are large enough to just allow a wire to go through each opening and electrically connect the balun to each layer 62a and 62b at points where the layers are at its closest distance, approximately 0.1 inches in this case, as it is well understood by those skilled in the art. In this configuration, the dimensions of substrate 64 are 4 inches long, 3 inches wide, and 0.27 inches thick. A maximum width of each layer 62a, 62b is approximately 2.7 inches, and a length of approximately 1.95 inches. The thickness of each layer 62a, 62b is typical of those previously described corresponding to a film or coating of conductive material applied to a dielectric substrate. Additionally, substrate 64 may have a dielectric permittivity somewhere between 1 and 150, and a tangent loss between 0 and 1.

In a typical evaluation of a material, the top surface of substrate 64, containing the bow-tie antenna, is conformally placed against the near, outer surface of the refractory material to launch EM waves, coming from computer-based processor 22, into the refractory wall and to receive reflected EM waves going back to computer-based processor 22. Those skill in the art will realize that layers 62a and 62b can be implemented by means of a variable conductivity material as described in previous embodiments of EM wave launcher 10. Likewise, the shape of layers 62a and 62b can be other than triangular, having straight edges, curved edges that follow a particular function, or a combination thereof.

Figure 7:
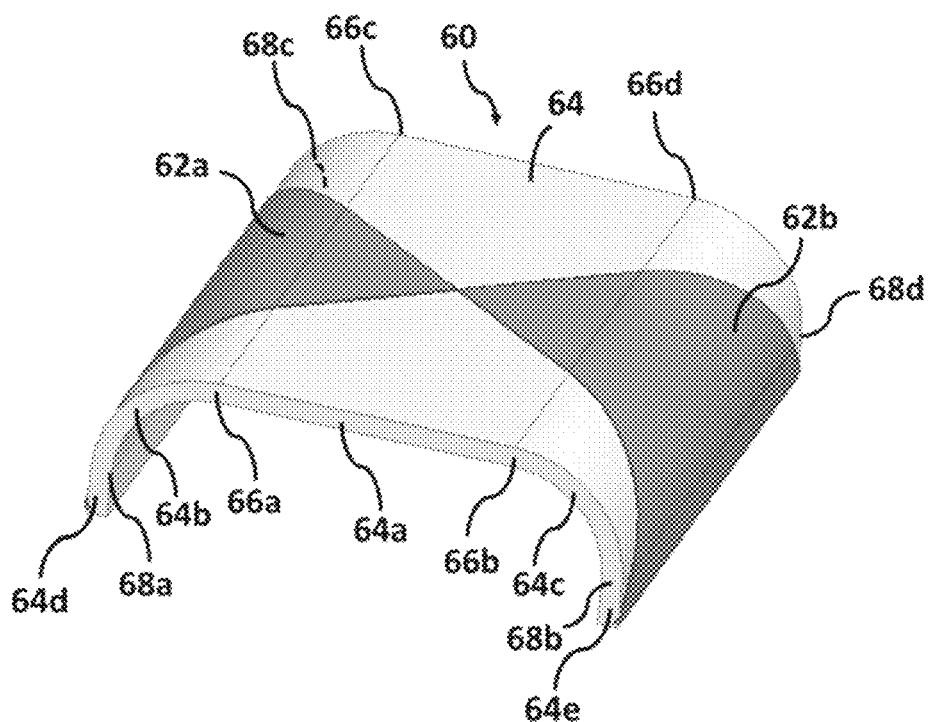
FIG. 7 shows a perspective view of a planar electromagnetic wave launcher with curved edges in accordance with another embodiment.

Similarly, FIG. 7 shows a configuration for planar EM wave launcher 60 of FIG. 6, having substrate 64 consisting of a first planar section 64a, a first curved-edge section 64b, a second curved-edge section 64c, a second planar section 64d, and a third planar section 64e. First planar section 64a extends over a plane from the bow-tie feeding area in a first dimension along the width of substrate 64 until reaching the width of substrate 64, in this case approximately 3 inches, and in a second dimension along the length of substrate 64 until reaching transition points 66a, 66b, 66c, and 66d; in this case, the distance between transition points 66a and 66b and between transition points 66c and 66d is approximately 4 inches.

As the first curved-edge section 64b and the second curved-edge section 64c extend away from the feeding point of the bow-tie antenna along the length of substrate 64, sections 64b and 64c bend towards the underside surface of substrate 64 following a circular path with a radius of curvature of approximately 1.6 inches for a quarter of circumference to reach transition points 68a, 68b, 68c, and 68d. In other words, the distance along the curved path of substrate 64 between transition points 66a and 68a is approximately 2.51 inches. This is substantially the same distance between transition points 66b and 68b, transition points 66c and 68c, and transition points 66d and 68d, respectively. Likewise, this is the same length of section 64b and section 64c along the curved path of substrate 64. At transition points 68a and 68c, second planar section 64d begins to extend the length of substrate 64 by approximately 0.5 inches. Correspondingly, at transition points 68b and 68d, third planar section 64e begins to extend the length of substrate 64 by approximately 0.5 inches. As such, second planar section 64d, and a third planar section 64e are substantially perpendicular to first planar section 64a.

In the configurations shown in FIGS. 6 and 7, the strongest clutter terms correspond to multiple reflections at the edges of the bow-tie antenna. The dimensions of the curved edges of the configuration of FIG. 7 are selected to extend the propagation time of the EM wave propagating on the surface of substrate 64 such that the time is longer than the propagation time of an EM wave propagating from the near, outer surface of the refractory wall to the remote, inner surface of the refractory wall. In this manner, the clutter effects associated with the multiple reflections of EM waves from the edges of the bow-tie antenna are significantly reduced. Those skilled in the art will realize that, in the configuration of FIG. 7, the edges of layers 64b and 64c may be tapered to follow an elliptical function, an exponential function, a smooth transitioning function, or any combination thereof. In addition, the length of sections 64d and 64e may be adjusted with the ultimate goal of reducing the clutter.

Furthermore, in each of the above-described configurations, a person of ordinary skill in the art will realize that a particular single signal processing method may be selected according to an estimated thickness of the material to be evaluated. For example, a signal processing method based on a Fourier Transform may be used to process the data received by computer-based processor 22, especially related to the evaluation of walls with thickness larger than 6 inches. On the other hand, signal processing methods based on super resolution algorithms would be preferred for evaluation of walls with thickness below 3 inches. Alternatively, a hybrid signal processing method comprised of one or more single signal processing methods may be used according to additional factors including the frequency of operation and bandwidth of the system, the temperature of operation of the furnace, and the type and quality of the refractory material.

Likewise, in each of the above-described configurations, the launching end of EM wave launcher 10 is, as discussed elsewhere in this specification, impedance matched to the material under evaluation, which further helps to suppress clutter.

Figure 8:
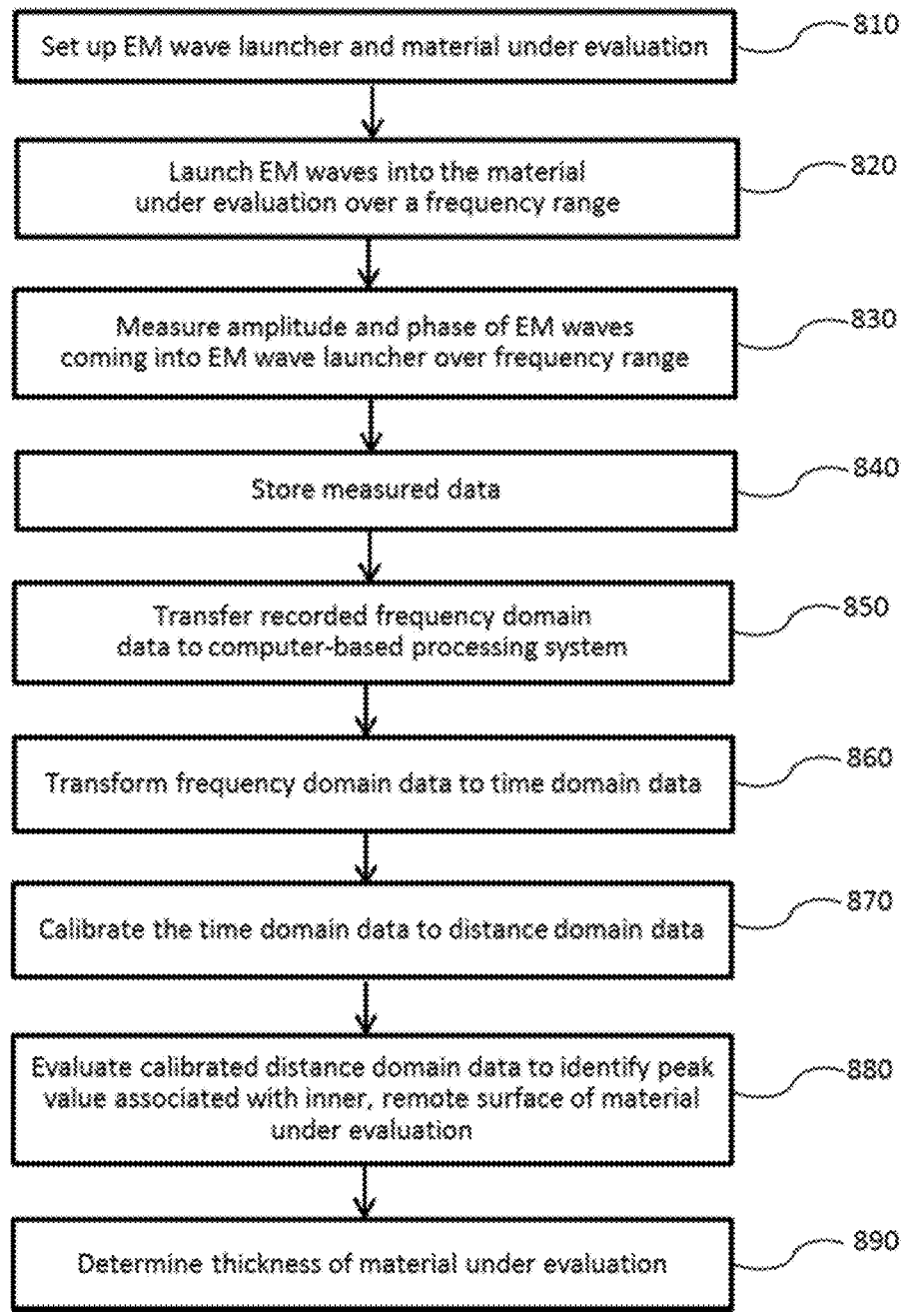
FIG. 8 shows a schematic view of a method for computing the thickness of a dielectric material according to any of the embodiments of the invention.

Regarding each of the above-described configurations, a method depicted in FIG. 8 for determining the thickness of the subject material under evaluation, such as refractory material, may be performed according to the following:

1. At step 810, setting up an EM wave launcher by placing a launching end of the EM wave launcher conformally contiguous to an outer, near surface of the material under evaluation to maximize physical contact, which corresponds to minimizing gaps, between the launching end of the EM wave launcher and the outer, near surface of the material under evaluation, such that upon operation of the EM launcher, EM waves are launched into the outer, near surface of the material under evaluation.

2. Next, at step 820, launching EM waves from the EM launcher into the outer surface of the material under evaluation by exciting EM wave propagating modes inside the EM wave launcher over a transmit frequency range, and correspondingly generating EM waves propagating inside the EM wave launcher from a feeding end of the EM wave launcher to the launching end of the EM wave launcher, over said frequency range.

3. Next, at step 830, measuring the amplitude and the phase of EM waves coming into the EM wave launcher over the frequency range, as a result of propagation of the EM waves launched by the EM wave launcher into the outer surface of the material under evaluation.

4. Next, at step 840, storing the measured amplitude and phase frequency domain data of the EM waves coming into the EM wave launcher.

5. Next, at step 850, transferring the recorded frequency domain data to a computer-based data processor.

6. Next, at step 860, transforming the recorded frequency domain data to time domain data by performing a mathematical inverse Fourier transform or other model-based inverse spectral transformation method, using the computer-based data processor.

7. Next, at step 870, calibrating the time domain data to distance domain data, according to the known or estimated phase velocity of the EM waves in the material under evaluation, and defining a reference point in a distance domain profile, based on a peak value over a clutter plus noise level of the calibrated distance domain data, that corresponds to the physical length between the feeding end of the EM wave launcher and the outer, near surface of the material under evaluation; wherein the reference point may be associated with an EM wave reflected into the EM wave launcher from the outer, near surface of the material under evaluation.

8. Next, at step 880, evaluating the calibrated distance domain data to identify a peak value, over the clutter plus noise level, between the reference point and a known original thickness of the material under evaluation, which may be associated with an EM wave reflected into the EM wave launcher from the inner, remote surface of the material under evaluation.

9. Last, at step 890, determining a distance from the identified peak value at step 880 to the reference point; the distance corresponding to the thickness of the material under evaluation (distance between the outer, near surface and the inner, remote surface of the material under evaluation).

Those of ordinary skill in the art will recognize that the steps above indicated can be correspondingly adjusted for specific configurations and other constraints such as measurement equipment, operating frequency band, type of EM wave launcher, operational conditions, surrounding environment, and available area and location for implementation of the material evaluation system for a given application. In particular, measurements of the amplitude and the phase of EM waves, required over a high dynamic range (in some cases in excess of 90 dB), may be accomplished in multiple ways, such as through use of a network analyzer, to measure the S11 scattering parameter, over a frequency band, using a monostatic configuration (a single device to both launch EM waves and receive EM waves) or to measure the S21 scattering parameter, over a frequency band, using a bistatic configuration (a first device to launch EM waves and a second device to receive EM waves).

Additionally, those skilled in the art will recognize that, while evaluating the calibrated distance domain data, intermediate peak values over the clutter plus noise level may appear between the reference point, associated with an EM wave reflected from the outer, near surface of the material under evaluation, and the peak value associated with an EM wave reflected from the inner, remote surface of the material under evaluation; it being understood that the intermediate peak values may be associated with flaws of the material under evaluation existing between the outer, near surface of the material under evaluation and the inner, remote surface of the material under evaluation.

Furthermore, the calibration of the time domain data to distance domain data includes the subtraction of the delay time (distance) associated with the EM wave launcher and cables. Moreover, the frequency dispersion effects of the EM wave launcher and the material under evaluation may be removed, if necessary, by normalizing the measured data of the material under evaluation with respect to another set of measured data corresponding to a reference configuration, by way of non-limiting example, of a known characteristic and thickness of a material similar to the material under evaluation, through processes well known to those skilled in the art.

Still further, it is noted that the material evaluation system as described in FIG. 1 operates in the frequency domain by launching EM waves at specific frequencies within the frequency band of interest. Then the recorded frequency domain data is transformed to time domain data for further processing. However, the system may be implemented to operate in the time domain as well. Preferably, in the time domain operation mode, the EM wave launcher may launch a plurality of EM waves in the frequency domain, such that the time domain representation of this plurality of EM waves corresponds to an RF waveform of short duration, for example a Gaussian, Rayleigh, Hermitian, Laplacian pulse or of the like or a combination thereof.

Alternatively, the EM wave launcher may be directly fed with such type of pulse by a time domain RF waveform generator. More preferably, the duration of the RF waveform is not larger than 5 nanoseconds. Accordingly, the EM wave launcher will transmit and receive time domain pulses and the system will measure the amplitude and time of arrival of these pulses, store the measured data, and transfer the stored data to the computer-based processing unit in the time domain. Then the steps may proceed of calibrating the time domain data to distance domain data, evaluating the calibrated domain data to identify the location of flaws on the inner, remote surface of the material under evaluation, and determining the thickness of the material under evaluation.

In each of the above-described configurations, as applicable, the length of the elongated section of the EM wave launcher 10 between the feeding end 12 and the portion of the launching end farthest away from the feeding end is selected to be long enough such that the multiple reflections corresponding to the eighth clutter term and other potential multiple reflections will arrive at the computer-based processor 22 distinctively later than any EM wave of interest. In this situation, the propagation time of an EM wave propagating along the EM wave launcher 10 is distinguishably larger than the propagation time of the EM wave propagating through the thickness of the refractory material under evaluation.

Accordingly, it is of utmost importance to configure the EM wave launcher 10 such that the time of receipt of an EM wave of interest, reflected from a remote discontinuity of the material under evaluation, is distinguishable from the time of receipt of spurious signals, reflected from the near surface of the material under evaluation. Hence, the length of the elongated section 16 of the EM wave launcher 10, between the feeding end and the portion of the launching end farthest away from the feeding end, may be shortened. The shortened length is selected to be short enough such that the multiple reflections corresponding to the eighth clutter term and other potential multiple reflections, including at least part of those corresponding to the fourth clutter term, will arrive at the computer-based processor earlier than any EM wave of interest. In this case, the propagation time of an EM wave propagating along the EM wave launcher 10 is distinguishably shorter than the propagation time of both the EM wave propagating through the thickness of the refractory material under evaluation and multiple reflections from the launching end 14.

Figure 9:
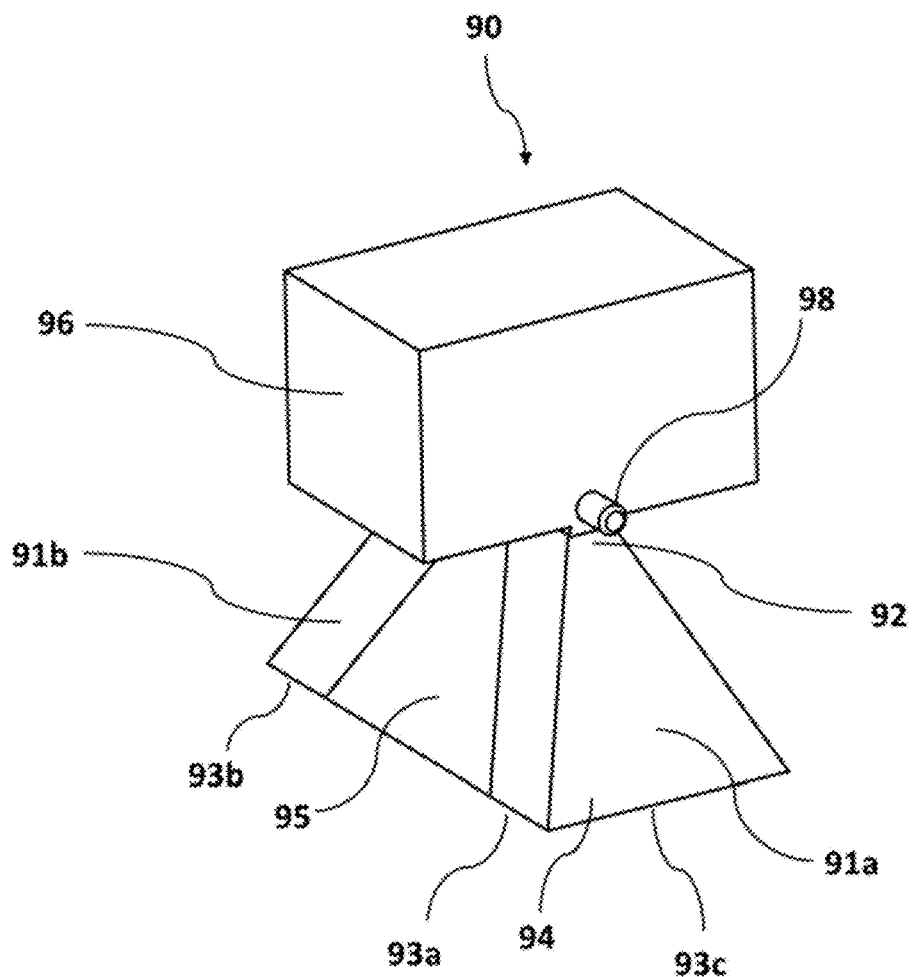
FIG. 9 shows a perspective view of an electromagnetic wave launcher in accordance with an embodiment of the invention.

FIG. 9 shows a perspective view of an EM wave launcher 90, comprising a feeding end 92 and a launching end 94. In particular, the length between feeding end 92 and launching end 94 is electrically small enough such that multiple EM wave reflections between launching end 94 and feeding end 92 arrive at a time distinguishably earlier than the time of arrival of any EM wave of interest. Likewise, multiple EM wave reflections from the near, outer wall of the refractory material under evaluation (not shown) will arrive at a time distinguishably earlier than the time of arrival of any EM wave of interest.

Feeding end 92 includes a feeding transition section 96 that electrically connects to a radiofrequency (RF) transmission line (not shown) through a coaxial connector 98. Accordingly, feeding transition section 96 consists of a coaxial cable fed cavity-backed feed. In particular, feeding transition section 96 is formed by an air-filled box of conductive material having rectangular cross-sections along each dimension of the box. The design characteristics of feeding transition section 96, corresponding to a coaxial cable fed cavity-backed feed with rectangular cross-sections, are well-known in the prior art and are equivalent to those of feeding transition section 18, as described above in reference to FIG. 3.

Accordingly, EM wave launcher 90 may be used in place of EM wave launcher 10 as indicated in the above-described embodiments, as applicable. More specifically, in this embodiment, EM wave launcher 90 consists of a modified pyramidal horn antenna with a rectangular cross section. EM wave launcher 90 structurally comprises a first flared plate 91a and a second flared plate 91b disposed opposite to plate 91a, like in a standard pyramidal horn antenna, having a rectangular cross section, in which the two opposite smaller plates are removed. In this configuration, first and second flared plates 91a, 91b are made of a conductive material.

The thickness of first and second flared plates 91a, 91b at launching end 94 defines a first edge 93a and a second edge 93b each of which may range in length from 0.05 to 1 inch. Preferably, the thickness of first and second flared plates 91a, 91b is uniform and the length of each edge 93a, 93b is at least 0.25 inch to smoothen the discontinuity experienced by an EM wave propagating along EM wave launcher and reaching a third edge 93c at launching end 94. Alternatively, one or more edges of first and second flared plates 91a, 91b may be rolled following an elliptical function or other smooth function to reduce the effects of edge reflections, as described above in reference to FIGS. 1 and 2A-2D. Moreover, the thickness of first and second flared plates 91a, 91b need not be uniform from feeding end 92 to launching end 94 and may have a variable thickness profile. Furthermore, first and second flared plates 91a, 91b of EM wave launcher 90 may comprise a material having a variable conductivity instead of being made of a conductive material, as described above in reference to FIGS. 2A-2D.

In this configuration, the volumetric region wherein the EM waves propagate within the EM wave launcher, in between first and second flared plates 91a, 91b, from feeding end 92 to launching end 94 is filled with a dielectric material 95, which may be air, liquid, or solid. Preferably, dielectric material 95 is a solid material having an impedance that substantially matches a predetermined impedance of the refractory material under the normal operating conditions of the furnace, as explained in the above-described embodiments, particularly in reference to FIGS. 2A-2D. Those skilled in the art will recognize that different shapes, sizes, and types of materials of dielectric material 95 may be used.

Preferably, EM wave launcher 90 is designed to operate in the frequency range from 0.25 GHz to 6 GHz. As a result, the dimensions of the rectangular cross section (width and height) at launching end 94 of EM wave launcher 90, the length of EM wave launcher 90, and the dielectric properties of the material occupying the internal volume of EM wave launcher 90 are all selected to enable EM wave launcher 10 to operate at this frequency range as well known in the prior art. In addition, EM wave launcher 90 is designed to tolerate the required temperature range of the near, outer surface of a furnace wall.

Optionally, EM wave launcher 90 can be used standalone (mono-static) or in array of more than one unit (multi-static) configuration, as described above in reference to FIG. 1 and well known in the prior art. Likewise, EM wave launcher 90 may be part of an entire material evaluation system packaged into a single portable unit, a single hand held unit, or integrated into a single assembly as described above.

With continued reference to FIG. 9, EM wave launcher 90 may be implemented to operate in a time domain-based material evaluation system. In this case, the length of flared plates 91a, 91b is preferably dimensioned such that the propagation time of a transmitted pulse from feeding end 92 to launching end 94 of EM wave launcher 90 is less than 1 nanosecond.

The various embodiments have been described herein in an illustrative manner, and it is to be understood that the terminology used is intended to be in the nature of words of description rather than of limitation. Any embodiment herein disclosed may include one or more aspects of the other embodiments. The exemplary embodiments were described to explain some of the principles of the present invention so that others skilled in the art may practice the invention. Obviously, many modifications and variations of the invention are possible in light of the above teachings. The present invention may be practiced otherwise than as specifically described within the scope of the appended claims and their legal equivalents.

We claim:

1. A system for evaluating a status of a material, comprising:
   a. an electromagnetic wave launcher having a first feeding end and a second launching end, wherein said first feeding end includes a feeding mechanism to excite an electromagnetic wave able to propagate through said electromagnetic wave launcher, wherein said second launching end is physically structured to reduce a plurality of reflections and probe ringing of said electromagnetic wave propagating through said launching end, by a sufficient extent so as to enable detection of an electromagnetic wave of interest reflected from a remote discontinuity of said material, wherein said electromagnetic wave launcher is provided a physical configuration to have an impedance at said second launching end that substantially matches an impedance of a near surface of said material, wherein said electromagnetic wave launcher is adapted to enable receipt of said electromagnetic wave of interest reflected from said remote discontinuity of said material within a time period sufficient to distinguish between said reflected electromagnetic wave of interest and reflected spurious signals from said near surface of said material, and wherein said launching end is adapted to be conformal to an area of said near surface of said material; and
   b. a computer-based processor having an executable computer code configured to: measure said reflected electromagnetic wave of interest to produce frequency domain data; transform said frequency domain data to time domain data; calibrate said time domain data to distance domain data; identify a peak in said distance domain profile associated with said electromagnetic wave of interest reflected from said material; and determine a distance traveled by said electromagnetic wave of interest reflected from said material.

2. The system of claim 1, said electromagnetic wave launcher further comprising a pyramidal horn antenna having a rectangular cross-section and comprising a first flared plate having a planar section and two flared sections along opposite side edges of said planar section of said first flared plate, and a second flared plate positioned opposite said first flared plate, said second flared plate comprising a planar section and two flared sections along opposite side edges of said planar section of said second flared plate.

3. The system of claim 1, wherein calibrating said time domain data to a distance domain data is performed by said computer executable code based upon a known velocity of a said electromagnetic wave of interest travelling through said material.

4. The system of claim 1, wherein said computer-based processor is adapted to visually display information about said status of said material based upon said distance traveled by said electromagnetic wave of interest reflected from said material.

5. The system of claim 1, wherein said status of said material is a thickness of said material.

6. The system of claim 1, wherein said status of said material is a flaw of said material.

7. The system of claim 1, wherein said electromagnetic wave launcher and at least one other component of said system are integrated into a single unit.

8. The system of claim 1, wherein said second launching end has at least one edge physically conformed to extend away from said area to be evaluated of said near surface of said material.

9. The system of claim 8, wherein said edge has a smooth rolled-edge configuration.

10. The system of claim 1, wherein said electromagnetic wave launcher is formed using a variable conductivity material disposed between said first feeding end and said second launching end, wherein said variable conductivity material has a first end closer to said first feeding end and a second end closer to said second launching end, and wherein said conductivity increases as a function of a distance from a point on said variable conductivity material to said second end of said variable conductivity material closer to said second launching end of said electromagnetic wave launcher.

11. The system of claim 1, wherein said first feeding end is adapted to reduce a plurality of reflections of said excited electromagnetic wave at said first feeding end, by a sufficient extent so as to reduce a level of clutter otherwise present in said system.

12. The system of claim 11, wherein said first feeding end further comprises a cavity-backed feeding pin.

13. The system of claim 1, said system further comprising an RF subsystem generating an electromagnetic wave in a frequency range of between 0.25 and 30 GHz.

14. The system of claim 1, wherein said electromagnetic wave launcher is adapted to shorten receipt of said reflected spurious signals from said near surface of said material by a time period sufficient to distinguish between said reflected electromagnetic wave of interest and said reflected spurious signals from said near surface of said material.

15. The system of claim 1, wherein said electromagnetic wave launcher is adapted to shorten receipt of reflected electromagnetic waves from a portion of said electromagnetic wave launcher by a time period sufficient to distinguish between said reflected electromagnetic wave of interest and said reflected electromagnetic waves from said portion of said electromagnetic wave launcher.

16. A method for evaluating a status of a material, comprising:
   a. providing an electromagnetic wave launcher having a first feeding end and a second launching end, wherein said first feeding end includes a feeding mechanism to excite an electromagnetic wave able to propagate through said electromagnetic wave launcher, wherein said second launching end is physically structured to reduce a plurality of reflections of said electromagnetic wave propagating through said launching end, by a sufficient extent so as to enable detection of an electromagnetic wave of interest reflected from a remote discontinuity of said material, wherein said electromagnetic wave launcher is provided a physical configuration to have an impedance at said second launching end that substantially matches an impedance of a near surface of said material, wherein said electromagnetic wave launcher is adapted to enable receipt of said electromagnetic wave of interest reflected from said remote discontinuity of said material within a time period sufficient to distinguish between said reflected electromagnetic wave of interest and reflected spurious signals from said near surface of said material, and wherein said launching end is adapted to be conformal to an area of said near surface of said material;

b. placing said launching end of said electromagnetic wave launcher conformally contiguous to said area of said near surface of said material to be evaluated;

c. launching a plurality of electromagnetic waves, propagating within a predetermined frequency range, onto said area to be evaluated of said near surface of said material;

d. detecting said electromagnetic wave of interest within said predetermined frequency range; and e. determining said status of said material based upon a determined distance traveled by said electromagnetic wave of interest reflected from said remote discontinuity of said material.

17. The method of claim 16, wherein said distance traveled by said electromagnetic wave of interest is determined based upon a time of travel of said electromagnetic wave of interest.

18. The method of claim 17, wherein said time of travel of said electromagnetic wave of interest is greater than a time of travel of said spurious signals by a sufficient extent so as to enable temporal isolation of said electromagnetic wave of interest from said spurious signals.

19. The method of claim 16, wherein a time domain representation of said plurality of electromagnetic waves propagating within a predetermined frequency range corresponds to a radiofrequency waveform of a short pulse duration.

20. The method of claim 19, wherein said radiofrequency waveform of short duration is selected from the group of a Gaussian pulse, a Rayleigh pulse, a Hermitian pulse, a Laplacian pulse, and a combination thereof.

21. The method of claim 19, wherein said duration of said radiofrequency waveform is not larger than 5 nanoseconds.

22. The method of claim 16, wherein determining said status of said material further comprising:
  a. measuring a set of data in time domain pertaining to said detected electromagnetic wave of interest;
  b. calibrating said time domain data to a distance domain data;
  c. identifying a peak in said distance domain data associated with said electromagnetic wave of interest reflected from said remote discontinuity of said material;
  d. determining a distance traveled by said electromagnetic wave of interest reflected from said remote discontinuity of said material; and
  e. determining a measurement of a distance from said near surface of said material to said remote discontinuity of said material based upon said distance traveled by said electromagnetic wave of interest reflected from said remote discontinuity of said material.

23. The method of claim 22, wherein calibrating said time domain data to said distance domain data is performed based upon a known propagation velocity of said electromagnetic wave of interest through said material.

24. The method of claim 16, wherein determining said status of said material further comprising:

a. measuring a set of data pertaining to said detected electromagnetic wave of interest;
  b. providing a first means for storing said set of data;
  c. providing a computer-based data processor for processing said set of data for evaluating said status of said material;
  d. transferring said set of data from said first means to said computer-based data processor; and
  e. processing said set of data by means of at least one signal processing method.

25. The method of claim 24, further comprising the step of processing said set of data utilizing a signal processing method selected according to a characteristic of said material to be evaluated.

26. The method of claim 16, wherein said status of said material is a thickness of said material.

27. The method of claim 16, further comprising the step of visually displaying information about said status of said material.

28. The method of claim 16, wherein said frequency range is between 0.25 and 30 GHz.

29. A method for evaluating a status of a material, comprising:
  a. providing an electromagnetic wave launcher having a first feeding end and a second launching end, wherein said first feeding end includes a feeding mechanism to excite an electromagnetic wave able to propagate through said electromagnetic wave launcher, wherein said second launching end is physically structured to reduce a plurality of reflections of said electromagnetic wave propagating through said launching end, by a sufficient extent so as to enable detection of a radiofrequency waveform of interest reflected from a remote discontinuity of said material, wherein said electromagnetic wave launcher is provided a physical configuration to have an impedance at said second launching end that substantially matches an impedance of a near surface of said material, wherein said electromagnetic wave launcher is adapted to enable receipt of said radiofrequency waveform of interest reflected from said remote discontinuity of said material within a time period sufficient to distinguish between said reflected radiofrequency waveform of interest and reflected spurious signals from said near surface of said material, and wherein said launching end is adapted to be conformal to an area of said near surface of said material;
  b. placing said launching end of said electromagnetic wave launcher conformally contiguous to said area of said near surface of said material to be evaluated;
  c. transmitting said radiofrequency waveform onto said area to be evaluated of said near surface of said material;
  d. detecting said radiofrequency waveform of interest; and
  e. determining said status of said material based upon a determined distance traveled by said radiofrequency waveform of interest reflected from said remote discontinuity of said material.

30. The method of claim 29, wherein said radiofrequency waveform has a short duration and is selected from the group of a Gaussian pulse, a Rayleigh pulse, a Hermitian pulse, a Laplacian pulse, and a combination thereof.

31. The method of claim 30, wherein said duration of said radiofrequency waveform is not larger than 5 nanoseconds.

32. The method of claim 29, wherein said distance traveled by said radiofrequency waveform of interest is determined based upon a time of travel of said radiofrequency waveform of interest.

33. The method of claim 32, wherein said time of travel of said radiofrequency waveform of interest is greater than a time of travel of said spurious signals by a sufficient extent so as to enable temporal isolation of said radiofrequency waveform of interest from said spurious signals.

34. The method of claim 29, wherein determining said status of said material further comprises:
   a. measuring a set of data in time domain pertaining to said detected radiofrequency waveform of interest;
   b. calibrating said time domain data to a distance domain data;
   c. identifying a peak in said distance domain data associated with said radiofrequency waveform of interest reflected from said remote discontinuity of said material;
   d. determining a distance traveled by said radiofrequency waveform of interest reflected from said remote discontinuity of said material; and
   e. determining a measurement of a distance from said near surface of said material to said remote discontinuity of said material based upon said distance traveled by said radiofrequency waveform of interest reflected from said remote discontinuity of said material.

35. The method of claim 34, wherein calibrating said time domain data to said distance domain data is performed based upon a known propagation velocity of said radiofrequency waveform of interest through said material.

36. The method of claim 29, wherein determining said status of said material further comprises:
   a. measuring a set of data pertaining to said detected radiofrequency waveform of interest;
   b. providing a first means for storing said set of data;
   c. providing a computer-based data processor for processing said set of data for evaluating said status of said material;
   d. transferring said set of data from said first means to said computer-based data processor; and
   e. processing said set of data by means of at least one signal processing method.

37. The method of claim 36, further comprising the step of processing said set of data utilizing a signal processing method selected according to a characteristic of said material to be evaluated.

38. The method of claim 29, wherein said status of said material is a thickness of said material.

39. The method of claim 29, further comprising the step of visually displaying information about said status of said material.

* * * * *